(12) United States Patent
Berezhnyy et al.

(10) Patent No.: US 10,327,952 B2
(45) Date of Patent: Jun. 25, 2019

(54) ULTRAVIOLET RADIATION SENSOR SYSTEMS AND METHODS FOR LASER PULSE ENERGY CONTROL IN EYE SURGERY

(71) Applicant: AMO Development, LLC, Santa Ana, CA (US)

(72) Inventors: Ihor Berezhnyy, Los Gatos, CA (US); Henry Price, San Jose, CA (US); Mark K. Lee, San Jose, CA (US)

(73) Assignee: AMO Development, LLC, Santa Ana, CA (US)

(*) Notice: Subject to any disclaimer, the term of this patent is extended or adjusted under 35 U.S.C. 154(b) by 2 days.

(21) Appl. No.: 15/693,200

(22) Filed: Aug. 31, 2017

(65) Prior Publication Data

US 2018/0055689 A1 Mar. 1, 2018

Related U.S. Application Data

(60) Provisional application No. 62/381,877, filed on Aug. 31, 2016.

(51) Int. Cl.
*A61F 7/00* (2006.01)
*A61F 9/008* (2006.01)
(Continued)

(52) U.S. Cl.
CPC ...... *A61F 9/00814* (2013.01); *A61F 9/00804* (2013.01); *A61N 5/06* (2013.01);
(Continued)

(58) Field of Classification Search
CPC ............ A61F 2009/00855; A61F 2009/00844
See application file for complete search history.

(56) References Cited

U.S. PATENT DOCUMENTS 4,665,913 A 5/1987 L'Esperance, Jr.
4,669,466 A 6/1987 L'Esperance, Jr.
(Continued)

OTHER PUBLICATIONS

"Stabilizing Scintillation Detector Systems: Determination of the Scintillator Temperature Exploiting the Temperature Dependence of the Light Pulse Decay Time" IEEE (2004) to Pausch.*

*Primary Examiner* — Kenneth J Malkowski
(74) *Attorney, Agent, or Firm* — Johnson & Johnson Surgical Vision, Inc.

(57) ABSTRACT

Systems are provided for delivering a calibrated ultraviolet radiation pulse at a treatment plane during a laser-ablation treatment of a patient's eye. Exemplary systems include an ultraviolet radiation source, and a fluorescent plate positioned to receive an initial ultraviolet radiation pulse produced by the ultraviolet radiation source. The fluorescent plate generates a visible light pulse in response to the initial ultraviolet radiation pulse. Exemplary systems further include a photon detector positioned to receive the visible light pulse for generating an electrical signal in response to the visible light pulse, and a processing module configured to determine an energy of the initial ultraviolet radiation pulse based on an amplitude and a decay time of the electrical signal, determine an energy calibration signal based on the determined energy of the initial ultraviolet radiation pulse, and provide the energy calibration signal to the ultraviolet radiation source for producing the calibrated ultraviolet radiation pulse.

16 Claims, 16 Drawing Sheets

(51) Int. Cl.
*A61N 5/06* (2006.01)
*A61B 17/00* (2006.01)
*A61B 18/00* (2006.01)

(52) U.S. Cl.
CPC ........... *A61B 2017/00066* (2013.01); *A61B 2018/00702* (2013.01); *A61B 2018/00714* (2013.01); *A61B 2018/00791* (2013.01); *A61F 2009/0088* (2013.01); *A61F 2009/00844* (2013.01); *A61F 2009/00848* (2013.01); *A61F 2009/00855* (2013.01); *A61F 2009/00872* (2013.01); *A61N 2005/0661* (2013.01)

(56) References Cited

U.S. PATENT DOCUMENTS

| | | |
|---|---|---|
| 4,732,148 A | 3/1988 | L'Esperance, Jr. |
| 4,770,172 A | 9/1988 | L'Esperance, Jr. |
| 4,773,414 A | 9/1988 | L'Esperance, Jr. |
| 5,108,388 A | 4/1992 | Trokel |
| 5,163,934 A | 11/1992 | Munnerlyn |
| 5,207,668 A | 5/1993 | L'Esperance, Jr. |
| 5,219,343 A | 6/1993 | L'Esperance, Jr. |
| 5,258,791 A | 11/1993 | Penney et al. |
| 5,646,791 A | 7/1997 | Glockler |
| 5,683,379 A | 11/1997 | Hohla |
| 5,713,892 A | 2/1998 | Shimmick |
| 5,807,379 A | 9/1998 | L'Esperance, Jr. |
| 6,000,800 A | 12/1999 | Webb et al. |
| 6,004,313 A | 12/1999 | Shimmick et al. |
| 6,095,651 A | 8/2000 | Williams et al. |
| 6,099,125 A | 8/2000 | Webb et al. |
| 6,203,539 B1 | 3/2001 | Shimmick et al. |
| 6,271,915 B1 | 8/2001 | Frey et al. |
| 6,315,413 B1 | 11/2001 | Shimmick et al. |
| 6,331,177 B1 | 12/2001 | Munnerlyn et al. |
| 2001/0056276 A1* | 12/2001 | LaHaye ............... A61B 18/20 606/5 |
| 2016/0022492 A1* | 1/2016 | Berezhnyy ........ A61F 9/00802 606/5 |

\* cited by examiner

ULTRAVIOLET RADIATION SENSOR SYSTEMS AND METHODS FOR LASER PULSE ENERGY CONTROL IN EYE SURGERY

CROSS REFERENCE TO RELATED APPLICATION

This application claims the benefit of U.S. Provisional Patent Application No. 62/381,877, filed Aug. 31, 2016, which is incorporated by reference as if fully set forth.

BACKGROUND

Embodiments of the present invention relate generally to the field of ultraviolet (UV) laser systems, and in particular encompass systems and methods for achieving a desired UV laser pulse energy during a laser vision correction treatment.

Setting the right energy for UV laser pulses at the treatment plane is an important step during a laser vision correction treatment. If the laser pulse energy does not have the desired parameters, it may be difficult to achieve the planned treatment outcome. Typically, setting the pulse energy involves two steps: measuring the energy of the UV laser pulse, and adjusting the energy of the UV laser pulse based on a previous energy measurement. A UV radiation sensor can be used to measure the energy of the UV laser pulse. Although currently known UV radiation sensors are helpful in achieving satisfactory performance in laser vision correction treatment systems, still further improvements in UV radiation sensor technology would be desirable. Embodiments of the present invention address these and other outstanding needs.

SUMMARY

Embodiments of the present invention provide UV radiation sensors that exhibit fast, accurate, and reliable pulse energy measurements, which are particularly useful as feedback for energy adjustment controls in vision correction treatment systems and other laser delivery modalities.

In a first aspect, embodiments of the present invention encompass systems for delivering a calibrated ultraviolet radiation pulse at a treatment plane during a laser-ablation treatment of a patient's eye. Exemplary systems may include an ultraviolet radiation source, and a fluorescent plate positioned to receive an initial ultraviolet radiation pulse produced by the ultraviolet radiation source. The position of the fluorescent plate may correlate to the treatment plane. The fluorescent plate may generate a visible light pulse in response to the initial ultraviolet radiation pulse. Exemplary systems may further include a photon detector positioned to receive the visible light pulse for generating an electrical signal in response to the visible light pulse, and a processing module comprising an input that receives the electrical signal, a processor, and a tangible non-transitory computer readable medium. The computer readable medium may be programmed with a computer application that, when executed by the processor, causes the processor to determine an energy of the initial ultraviolet radiation pulse based on an amplitude and a decay time of the electrical signal, determine an energy calibration signal based on the determined energy of the initial ultraviolet radiation pulse, and provide the energy calibration signal to the ultraviolet radiation source for producing the calibrated ultraviolet radiation pulse. In some cases, the decay time of the electrical signal may correlate with a temperature of the fluorescent plate, and the computer application, when executed by the processor, may cause the processor to determine the energy of the initial ultraviolet radiation pulse based on the amplitude and the decay time of the electrical signal by determining the temperature of the fluorescent plate based on the decay time of the electrical signal, determining a temperature adjustment coefficient based on the temperature of the fluorescent plate, and determining the energy of the initial ultraviolet radiation pulse based on the amplitude of the electrical signal and the temperature adjustment coefficient. In some cases, the computer application, when executed by the processor, may cause the processor to determine the temperature of the fluorescent plate and the temperature adjustment coefficient using an algorithm. The algorithm may correlate the decay time and the temperature adjustment coefficient with the temperature of the fluorescent plate. In some cases, the fluorescent plate comprises pure sapphire or doped sapphire.

In another aspect, embodiments of the present invention encompass ultraviolet radiation sensors for measuring an energy of an ultraviolet radiation pulse. Exemplary ultraviolet radiation sensors may include a fluorescent plate for receiving an ultraviolet radiation pulse and generating a visible light pulse in response to the ultraviolet radiation pulse. Exemplary ultraviolet radiation sensors may further include a photon detector positioned to receive the visible light pulse for generating an electrical signal in response to the visible light pulse, and a processing module. The processing module may include an input for receiving the electrical signal, a processor, and a tangible non-transitory computer readable medium. The computer readable medium may be programmed with a computer application that, when executed by the processor, causes the processor to determine an amplitude and a decay time of the electrical signal, and determine an energy of the ultraviolet radiation pulse based on the amplitude and the decay time of the electrical signal. In some instances, the computer readable medium may store an algorithm for correlating the decay time with the temperature of the fluorescent plate and correlating a temperature adjustment coefficient with the temperature of the fluorescent plate. The computer application, when executed by the processor, may cause the processor to use the algorithm to determine the energy of the ultraviolet radiation pulse based on the amplitude and the decay time of the electrical signal by determining the temperature of the fluorescent plate based on the decay time, determining the temperature adjustment coefficient based on the temperature of the fluorescent plate, and determining the energy of the ultraviolet radiation pulse based on the amplitude of the electrical signal and the temperature adjustment coefficient. In some instances, the fluorescent plate may comprise pure sapphire or doped sapphire. In other instances, the fluorescent plate may comprise yttrium oxide (Y2O3) doped with rare-earth ions. In some instances, the ultraviolet radiation sensor may further include an optical interface positioned between the fluorescent plate and the photon detector for blocking ultraviolet radiation and transmitting visible light.

In another aspect, embodiments of the present invention encompass methods of measuring an energy of an ultraviolet radiation pulse. Exemplary methods may include converting the ultraviolet radiation pulse into a visible light pulse using a fluorescent plate, and converting the visible light pulse into an electrical signal using a photon detector. The methods may further include determining, using a processing module comprising an input for receiving the electrical signal, a processor, and a tangible non-transitory computer readable medium, an amplitude and a decay time of the electrical signal. The methods may further include determining, using the processing module, the energy of the ultraviolet radiation pulse based on the amplitude and the decay time of the electrical signal. In some cases, the decay time of the electrical signal may correlate with a temperature of the fluorescent plate, and determining the energy of the ultraviolet radiation pulse may include determining the temperature of the fluorescent plate based on the decay time, determining a temperature adjustment coefficient based on the temperature, and determining the energy of the ultraviolet radiation pulse based on the amplitude of the electrical signal and the temperature adjustment coefficient. In some cases, the computer readable medium may store an algorithm for correlating the decay time and the temperature adjustment coefficient with the temperature of the fluorescent plate, and determining the temperature of the fluorescent plate and determining the temperature adjustment coefficient may be performed using the algorithm. In some cases, the fluorescent plate may comprise pure or doped sapphire. In some cases, the fluorescent plate may comprise yttrium oxide (Y2O3) doped with rare-earth ions.

In another aspect, embodiments of the present invention encompass methods of delivering a calibrated ultraviolet radiation pulse at a treatment plane during a laser-ablation treatment of a patient's eye. Exemplary methods may include producing an initial ultraviolet radiation pulse using an ultraviolet radiation source, converting the initial ultraviolet radiation pulse into a visible light pulse using a fluorescent plate, and converting the visible light pulse into an electrical signal using a photon detector. The methods may further include determining, using a processing module comprising an input for receiving the electrical signal, a processor and a tangible non-transitory computer readable medium, an amplitude and a decay time of the electrical signal. The methods may further include determining, using the processing module, an energy of the initial ultraviolet radiation pulse based on the amplitude and the decay time of the electrical signal, determining, using the processing module, an energy calibration signal based on the determined energy of the initial ultraviolet radiation pulse, and providing the energy calibration signal to the ultraviolet radiation source for producing the calibrated ultraviolet radiation pulse. In some cases, the decay time of the electrical signal may correlate with a temperature of the fluorescent plate, and determining the energy of the initial ultraviolet radiation pulse may include determining the temperature of the fluorescent plate based on the decay time of the electrical signal, determining a temperature adjustment coefficient based on the temperature of the fluorescent plate, and determining the energy of the initial ultraviolet radiation pulse based on the amplitude of the electrical signal and the temperature adjustment coefficient. In some cases, the computer readable medium may store an algorithm for correlating the decay time and the temperature adjustment coefficient with the temperature of the fluorescent plate, and determining the temperature of the fluorescent plate and determining the temperature adjustment coefficient may be performed using the algorithm. In some cases, the fluorescent plate may comprise pure or doped sapphire.

In another aspect, embodiments of the present invention encompass ultraviolet radiation sensors. Exemplary ultraviolet sensors may include a sapphire plate for receiving an ultraviolet radiation pulse and generating a visible light pulse in response to the ultraviolet radiation pulse, an optical interface positioned to block ultraviolet radiation and transmit the visible light pulse, a photon detector positioned to receive the visible light pulse for generating an electrical signal in response to the visible light pulse, and a processing module that may include an input for receiving the electrical signal, a processor and a tangible non-transitory computer readable medium. The computer readable medium may be programmed with a computer application that, when executed by the processor, may cause the processor to determine an amplitude and a decay time of the electrical signal, and determine an energy of the ultraviolet radiation pulse based on the amplitude and the decay time of the electrical signal.

In another aspect, embodiments of the present invention encompass devices for simultaneously measuring an energy of an ultraviolet radiation pulse and a temperature associated with the devices. Exemplary devices may include a fluorescent plate for receiving the ultraviolet radiation pulse and generating a visible light pulse in response to the ultraviolet radiation pulse, and a photon detector positioned to receive the visible light pulse for generating an electrical signal in response to the visible light pulse. The devices may further include a processing module that may include an input for receiving the electrical signal, a processor and a tangible non-transitory computer readable medium. The computer readable medium may be programmed with a computer application that, when executed by the processor, may cause the processor to determine an amplitude and a decay time of the electrical signal, determine a temperature of the fluorescent plate based on the decay time, determine a temperature adjustment coefficient based on the temperature of the fluorescent plate, and determine the energy of the ultraviolet radiation pulse based on the amplitude and the temperature adjustment coefficient.

In another aspect, embodiments of the present invention encompass methods for simultaneous measurement of an energy of an ultraviolet radiation pulse and a temperature associated with a fluorescent plate. Exemplary methods may include converting the ultraviolet radiation pulse into a visible light pulse using the fluorescent plate, converting the visible light pulse into an electrical signal using a photon detector, and determining, using a processing module comprising an input for receiving the electrical signal, a processor, and a tangible non-transitory computer readable medium, an amplitude and a decay time of the electrical signal. The methods may further include determining, using the processing module, a temperature of the fluorescent plate based on the decay time of the electrical signal, determining, using the processing module, a temperature adjustment coefficient based on the temperature of the fluorescent plate, and determining, using the processing module, the energy of the ultraviolet radiation pulse based on the amplitude of the electrical signal and the temperature adjustment coefficient.

In another aspect, embodiments of the present invention encompass devices for performing drift-free measurement of an energy of an ultraviolet radiation pulse. Exemplary devices may include a fluorescent plate for receiving the ultraviolet radiation pulse and generating a visible light pulse in response to the ultraviolet radiation pulse, a photon detector positioned to receive the visible light pulse for generating an electrical signal in response to the visible light pulse, and a processing module that may include an input for receiving the electrical signal, a processor and a tangible non-transitory computer readable medium. The computer readable medium may be programmed with a computer application that, when executed by the processor, may cause the processor to determine an amplitude and a decay time of the electrical signal, and determine the energy of the ultraviolet radiation pulse based on the amplitude and the decay time of the electrical signal. In some cases, the determined energy of the ultraviolet radiation pulse may not be susceptible to degradation over time.

In another aspect, embodiments of the present invention encompass methods for drift-free measurement of an energy of an ultraviolet radiation pulse. Exemplary methods may include converting the ultraviolet radiation pulse into a visible light pulse using a fluorescent plate, converting the visible light pulse into an electrical signal using a photon detector, and determining, using a processing module that may include an input for receiving the electrical signal, a processor, and a tangible non-transitory computer readable medium, an amplitude and a decay time of the electrical signal. The methods may further include determining, using the processing module, the energy of the ultraviolet radiation pulse based on the amplitude and the decay time of the electrical signal. In some cases, the determined energy of the ultraviolet radiation pulse may not be susceptible to degradation over time.

In another aspect, embodiments of the present invention encompass devices for measuring an energy of an ultraviolet radiation pulse without reduction in sensitivity. Exemplary devices may include a fluorescent plate for receiving the ultraviolet radiation pulse and generating a visible light pulse in response to the ultraviolet radiation pulse, a photon detector positioned to receive the visible light pulse for generating an electrical signal in response to the visible light pulse, and a processing module that may include an input for receiving the electrical signal, a processor and a tangible non-transitory computer readable medium. The computer readable medium may be programmed with a computer application that, when executed by the processor, may cause the processor to determine an amplitude and a decay time of the electrical signal, and determine the energy of the ultraviolet radiation pulse based on the amplitude and the decay time of the electrical signal. In some cases, a sensitivity of the fluorescent plate in response to ultraviolet radiation may not be susceptible to degradation over time.

In another aspect, embodiments of the present invention encompass methods for performing measurement of an energy of an ultraviolet radiation pulse without reduction in sensitivity. Exemplary methods may include converting the ultraviolet radiation pulse into a visible light pulse using a fluorescent plate, converting the visible light pulse into an electrical signal using a photon detector, and determining, using a processing module that may include an input for receiving the electrical signal, a processor, and a tangible non-transitory computer readable medium, an amplitude and a decay time of the electrical signal. The methods may further include determining, using the processing module, the energy of the ultraviolet radiation pulse based on the amplitude and the decay time of the electrical signal. In some cases, a sensitivity of the fluorescent plate in response to ultraviolet radiation may not be susceptible to degradation over time.

In another aspect, embodiments of the present invention encompass devices for measuring an energy of an ultraviolet radiation pulse by detecting an entire fluorescent profile induced by the ultraviolet radiation pulse. Exemplary devices may include a sapphire plate for receiving the ultraviolet radiation pulse and generating a fluorescent light pulse in response to the ultraviolet radiation pulse, a photon detector positioned to receive the fluorescent light pulse for generating an electrical signal in response to the fluorescent light pulse, and a processing module that may include an input for receiving the electrical signal, a processor and a tangible non-transitory computer readable medium. The computer readable medium may be programmed with a computer application that, when executed by the processor, may cause the processor to detect an entire profile of the electrical signal as a function of time, determine an amplitude and a decay time of the electrical signal based on the entire profile of the electrical signal as a function of time, and determine the energy of the ultraviolet radiation pulse based on the amplitude and the decay time of the electrical signal. In some cases, the entire profile of the electrical signal as a function of time may correlate with an entire profile of the fluorescent light pulse induced by the ultraviolet radiation pulse.

In another aspect, embodiments of the present invention encompass methods of measuring an energy of an ultraviolet radiation pulse by detecting an entire fluorescent profile induced by the ultraviolet radiation pulse. Exemplary methods may include converting the ultraviolet radiation pulse into a fluorescent light pulse using a fluorescent plate, converting the fluorescent light pulse into an electrical signal using a photon detector, detecting, using a processing module that may include an input for receiving the electrical signal, a processor, and a tangible non-transitory computer readable medium, an entire profile of the electrical signal as a function of time, determining, using the processing module, an amplitude and a decay time of the electrical signal based on the entire profile of the electrical signal as a function of time, and determining, using the processing module, the energy of the ultraviolet radiation pulse based on the amplitude and the decay time of the electrical signal. In some cases, the entire profile of the electrical signal as a function of time may correlate with an entire profile of the fluorescent light pulse induced by the ultraviolet radiation pulse.

In another aspect, embodiments of the present invention encompass methods of compensating an energy reading for a ultraviolet radiation pulse utilizing a fluorescent decay time as a temperature sensor. Exemplary methods may include converting the ultraviolet radiation pulse into a visible light pulse using a fluorescent plate, converting the visible light pulse into an electrical signal using a photon detector, determining, using a processing module that may include an input for receiving the electrical signal, a processor, and a tangible non-transitory computer readable medium, an amplitude and a decay time of the electrical signal, determining, using the processing module, a temperature of the fluorescent plate based on the decay time of the electrical signal, determining, using the processing module, a temperature adjustment coefficient based on the temperature of the fluorescent plate, and scaling, using the processing module, the amplitude of the electrical signal using the temperature adjustment coefficient to obtain a temperature-compensated energy reading for the ultraviolet radiation pulse.

For a fuller understanding of the nature and advantages of the present invention, reference should be had to the ensuing detailed description taken in conjunction with the accompanying drawings.

DETAILED DESCRIPTION OF THE PREFERRED EMBODIMENTS

Embodiments of the present invention can be particularly useful for enhancing the accuracy and efficacy of laser eye surgical procedures, such as photorefractive keratectomy (PRK), phototherapeutic keratectomy (PTK), and the like. In some instances, embodiments of the present invention can provide enhanced accuracy of refractive procedures that involve removal or sculpting of the cornea or modification of other opthalmological tissues or structures. Hence, while the system and methods of exemplary embodiments of the present invention are described primarily in the context of a laser eye surgery system for treating a cornea of the eye, it should be understood the techniques of the present invention may be adapted for use in alternative ablation procedures and other laser delivery processes.

The techniques disclosed herein can be readily adapted for use with existing laser systems. By providing a more accurate (and hence, for example, less error-prone) methodology for treating optical errors of an eye, embodiments of the present invention facilitate sculpting of the cornea or other opthalmological tissues so that treated eyes may consistently and reliably receive a desired optical correction imparting improved vision.

Figure 1:
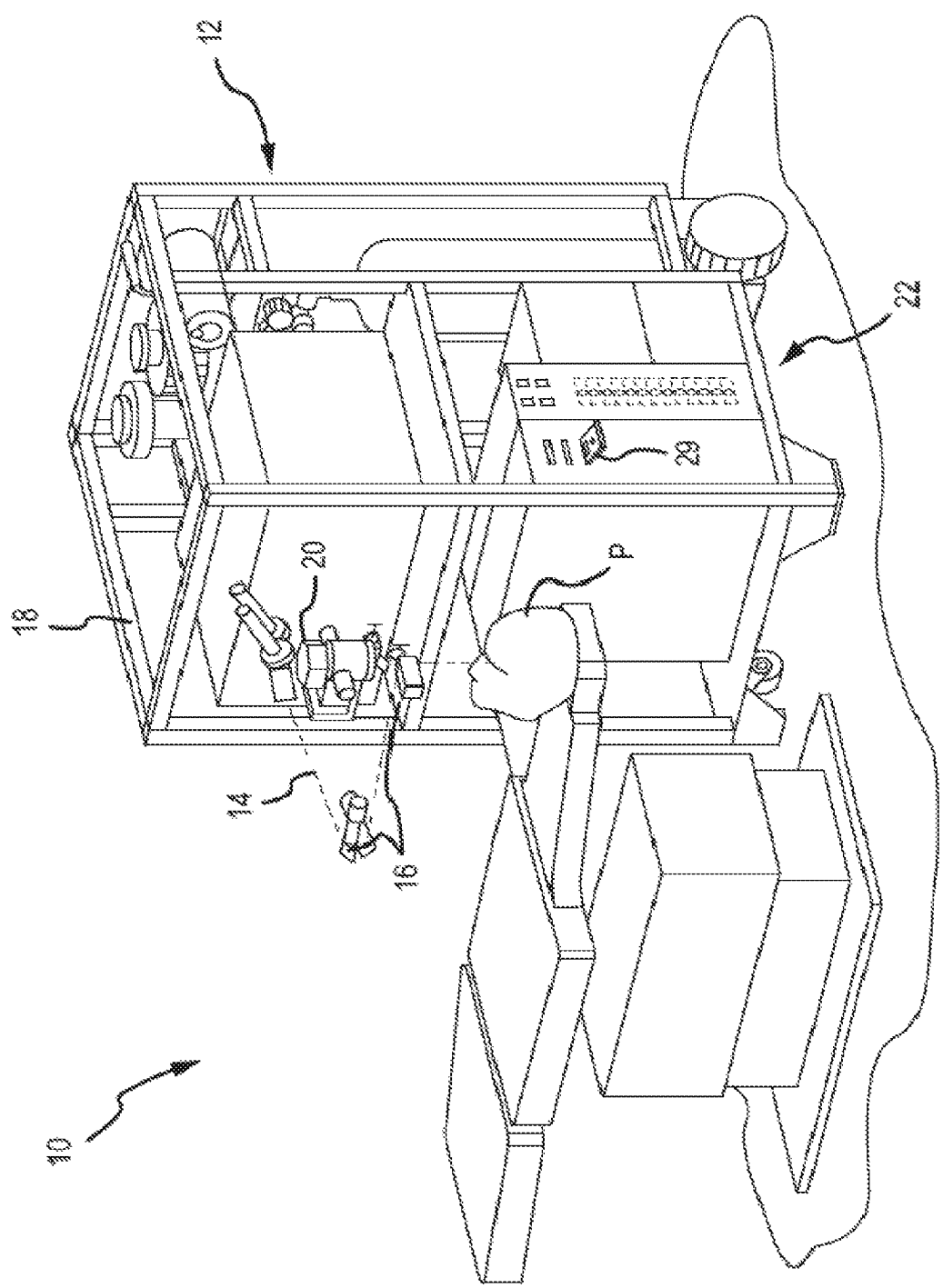
FIG. 1 illustrates a laser ablation system according to an embodiment of the present invention.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with an input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
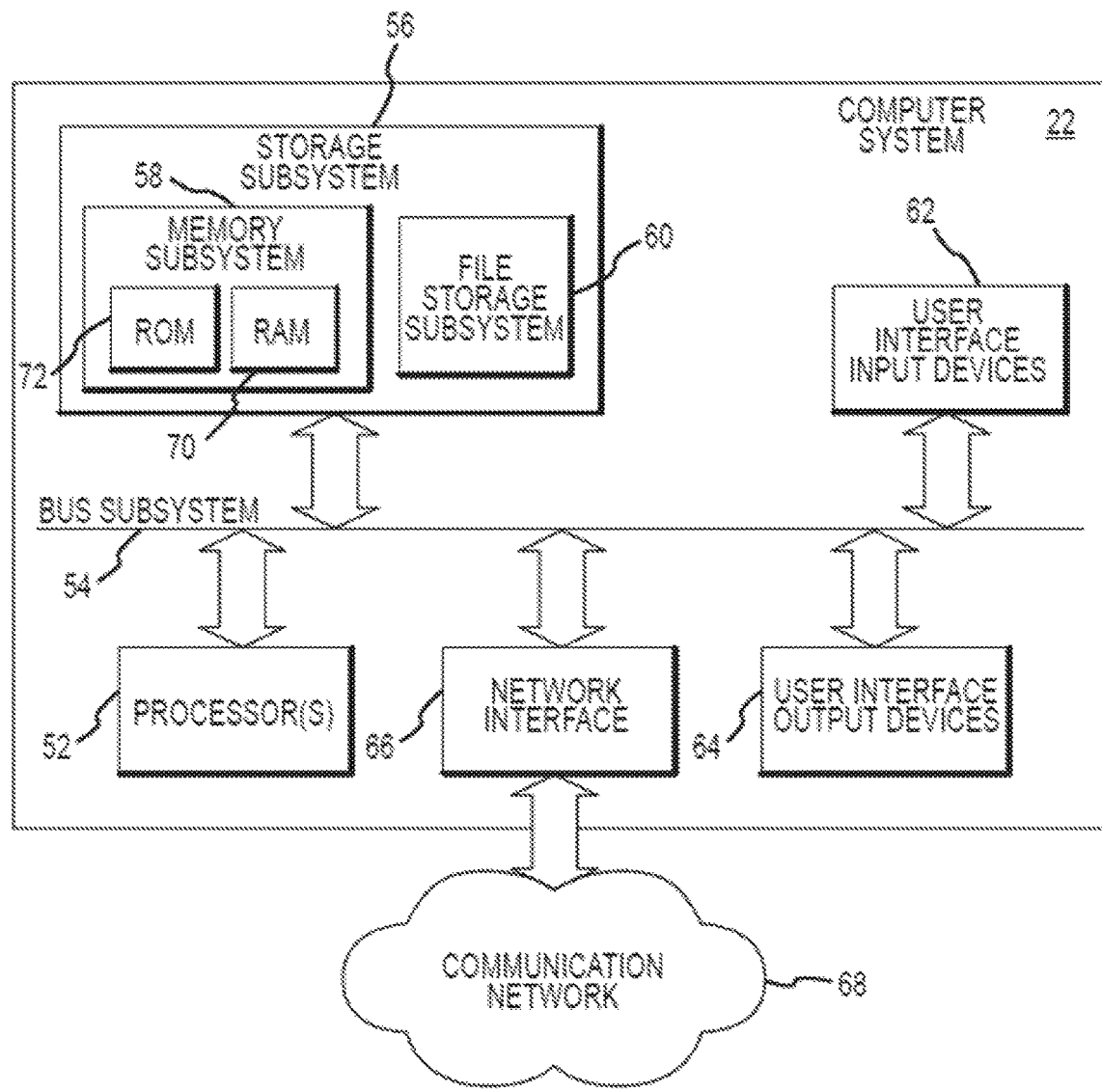
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touch-screen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as desired. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
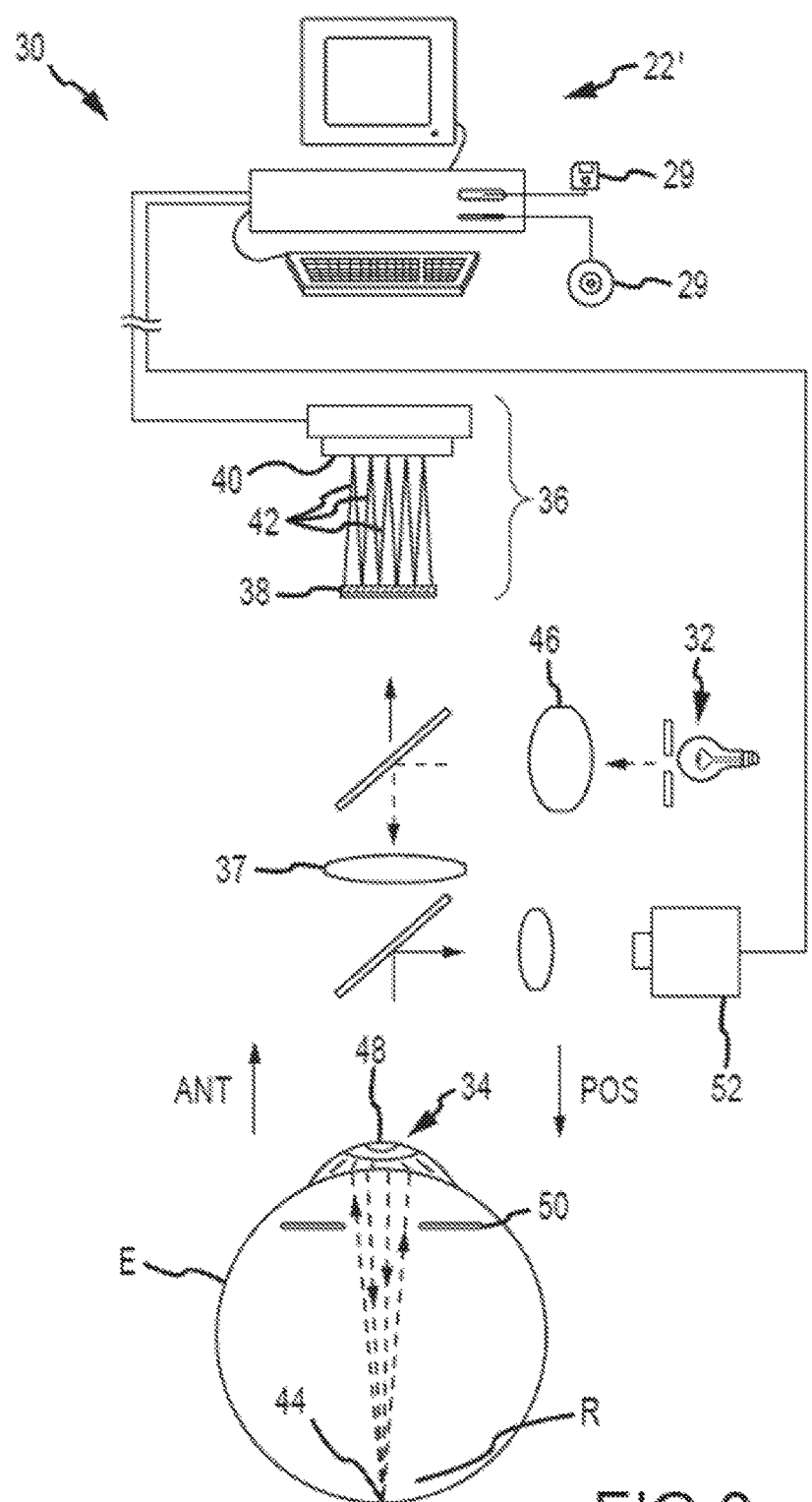
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via a networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
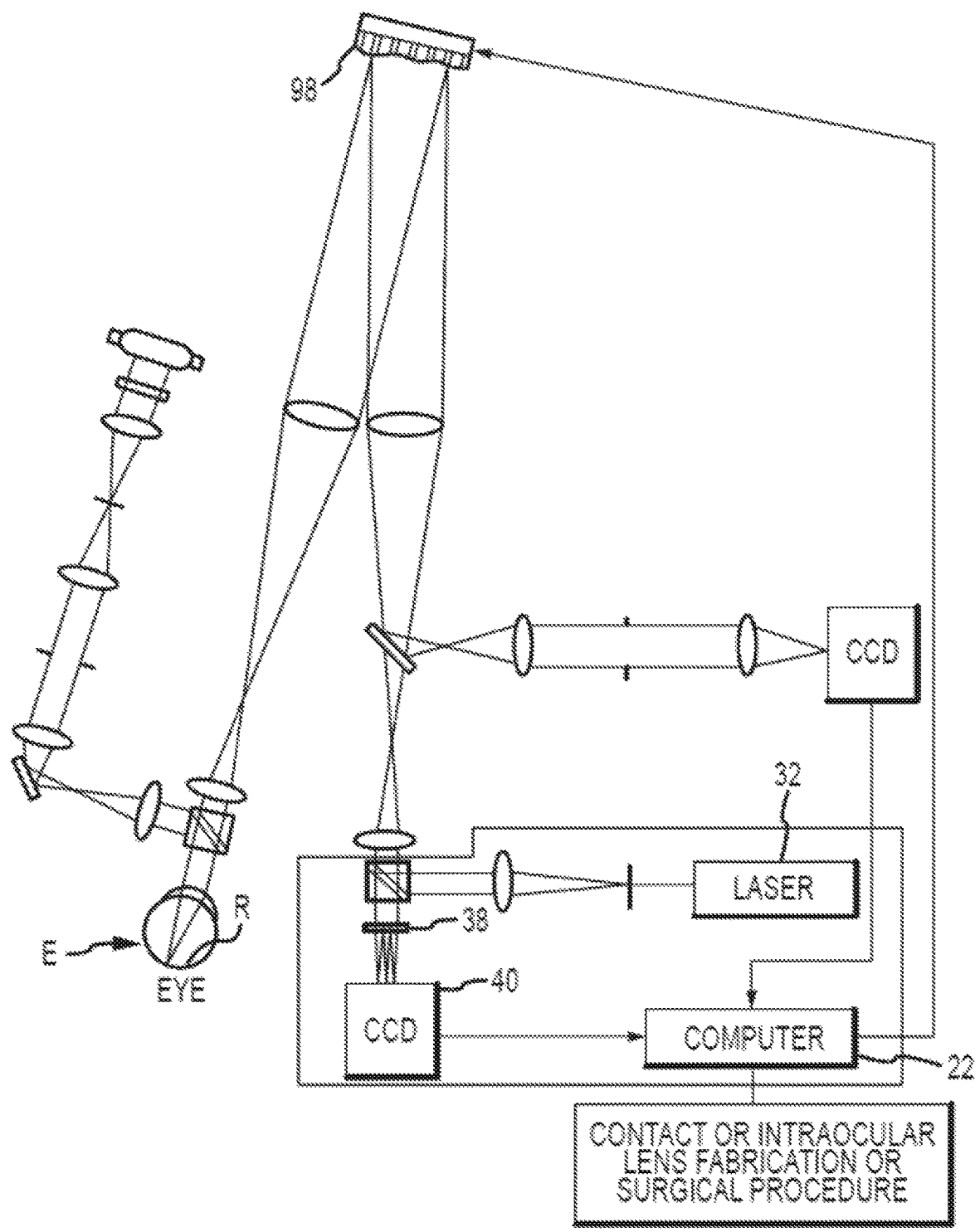
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror 98. The source image is reflected from deformable mirror 98 during transmission to retina R, and the deformable mirror 98 is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from AMO Manufacturing USA, LLC, Milpitas, Calif. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by Abbott Medical Optics, Inc., including the iDesign system, and the like.

Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like. Embodiments of the present invention may also involve wavefront measurement schemes such as a Tscherning-based system, which may be provided by WaveFront Sciences, Inc. Embodiments of the present invention may also involve wavefront measurement schemes such as a ray tracing-based system, which may be provided by Tracey Technologies, Corp.

Setting the desired energy for an ultraviolet (UV) laser pulse at the treatment plane is an important step in preparing a laser vision correction system for delivering a treatment to a patient. Having an incorrect pulse energy can change the planned treatment outcome or make it otherwise difficult to obtain an effectively therapeutic outcome for the patient. Setting the energy typically involves two steps: energy measurement, and energy adjustment based on last energy measurement. A UV radiation sensor is a device that is used to measure the energy of the UV laser pulse. Embodiments of the present invention encompass UV radiation sensors that provide fast (e.g. from milliseconds to microseconds level, depending on laser repetition rate), accurate, and reliable measurements as feedback for energy adjustment controls.

Figure 4:
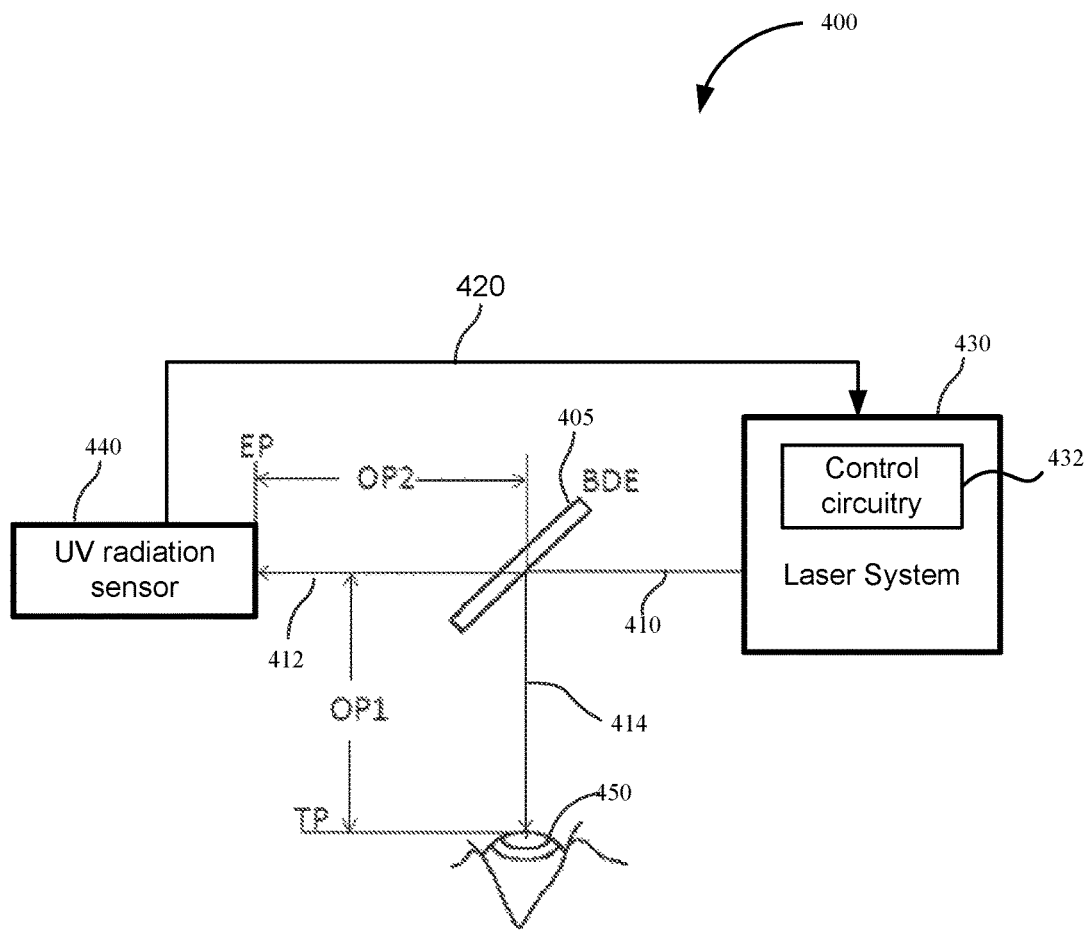
FIG. 4 illustrates schematically an exemplary laser vision treatment system according to an embodiment of the present invention.

FIG. 4 schematically illustrates an exemplary laser vision treatment system according to an embodiment of the present invention. As illustrated in FIG. 4, a laser beam 410 from a laser system 430 may be sent through a beam dividing element (BDE) 405 such that a first portion 412 of the beam 410 can be sent to the UV radiation sensor 440 along optical path 2 (OP2). A second portion 414 of the original laser beam 410 may go through optical path 1 (OP1) to be delivered onto the patient's cornea 450 situated at the treatment plane (TP). The term "ultraviolet radiation" as used herein can refer to electromagnetic radiation with a wavelength that is shorter than that of visible light but longer than that of X-rays. For example, it may refer to electromagnetic radiation with a wavelength from about 10 nm to about 380 nm.

In some embodiments, the UV radiation sensor 440 may be located at the same distance from the BDE 405 as the treatment plane TP. In other words, the UV radiation sensor 440 may be located such that distance OP2 between the point at which the laser beam 410 passes through the BDE 405 and the UV radiation sensor 440 is the same as distance OP1 between the point at which the laser beam 410 is reflected to the treatment plane TP. The laser spot at the UV radiation sensor 440 may be identical in shape to the laser spot at the treatment plane (TP). Additionally, the laser spot at the UV radiation sensor 440 may be scaled by a scale factor as compared with the laser spot at the treatment plane TP. The scale factor may depend on transmission and reflection properties of the beam dividing element 405.

While the laser system 430 is illustrated as part of an ophthalmic surgery laser system, it should be understood that methods and devices disclosed herein may be used in other laser systems where it is desirable to measure beam energy.

Embodiments disclosed herein may provide real-time measurement of laser pulse energy. Real-time measurement may be advantageous as it allows for monitoring of a treatment in real time and, if needed, revision of the treatment parameters in real time when deviations from a desired treatment are identified. For example, the UV radiation sensor 440 may send a feedback signal 420 to the laser system 430, and a control circuitry 432 of the laser system 430 may adjust the laser pulse energy in response to the feedback signal 420. The techniques provided herein allow for compensating for temperature changes in at least a part of the UV radiation sensor 440 in order to achieve more accurate measurements of energy of the UV radiation.

Figure 5:
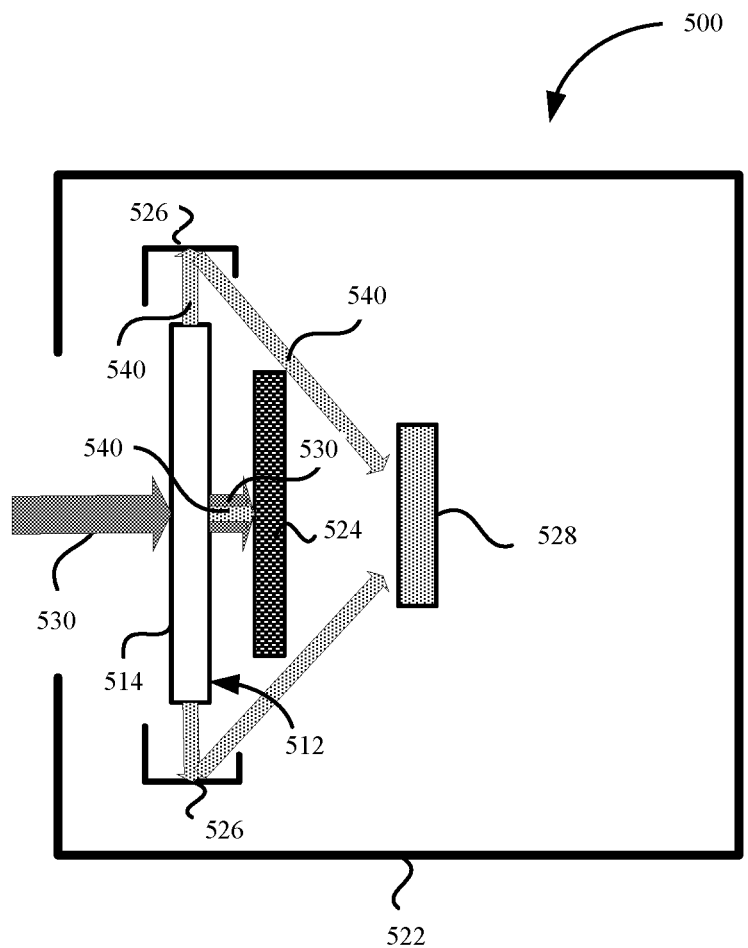
FIG. 5 illustrates schematically an exemplary UV radiation sensor according an embodiment of the present invention.

FIG. 5 schematically illustrates a UV radiation sensor 500 according an embodiment of the present invention. The UV radiation sensor 500 may include a housing 522 for housing a UV-to-visible converter 514, a light blocker 524, a conical mirror 526, and a photon detector 528. A laser beam 530 falls on the UV-to-visible converter plate 514 and causes the UV-to-visible converter plate 514 to emit fluorescent light 540 in the visible range. Fluorescent light 540 propagates in all directions including directions toward the edge of the converter plate 514. The light blocker 524 may be positioned adjacent to a back surface 512 of the converter plate 514 and may be configured to block ambient light in the environment from reaching the photon detector 528. The light blocker 524 may also prevent UV light transmitted through the UV-to-visible converter 514, as well as fluorescent light emitted through the back surface 512 of the UV-to-visible converter 514, from traveling past the blocker 524. The fluorescent light 540 that is emitted from the edge of the converter plate 514 is redirected by the conical mirror 526 toward the photon detector 528, thereby bypassing the light blocker 524. The laser beam 530 emitted from the back surface 512 of the UV-to-visible converter plate 514 includes some UV radiation even though some visible fluorescent light 540 is also emitted in that direction. The reference numeral 530 pointing to this light emitted from the back surface 512 of the UV-to-visible converter plate 514 indicates the substantially unchanged nature of at least a portion of light emitted from the back surface 512.

Figure 6:
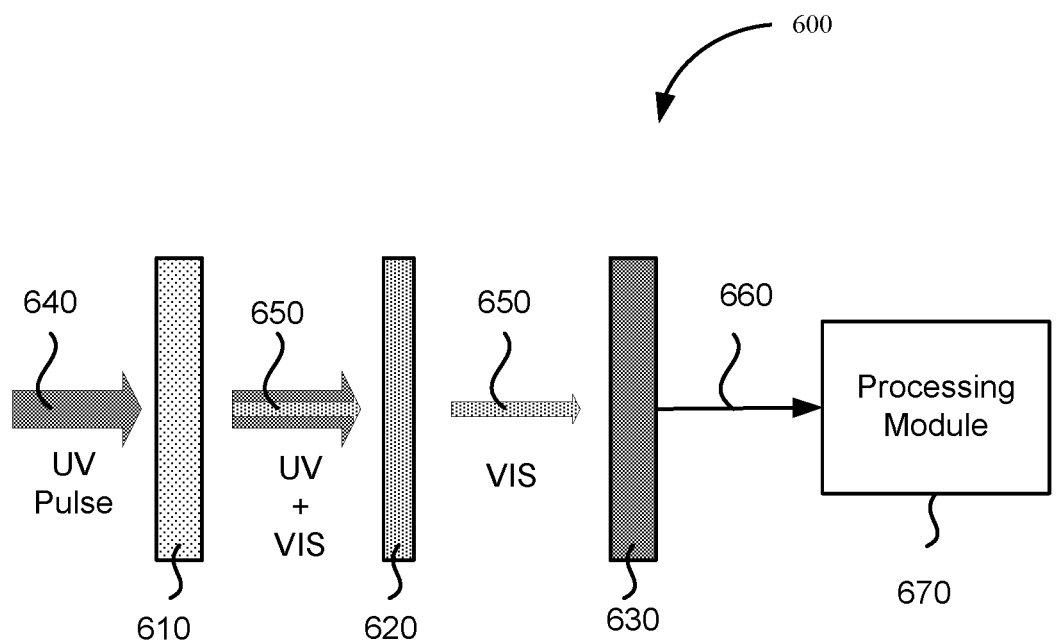
FIG. 6 illustrates schematically an exemplary UV radiation sensor according to another embodiment of the present invention.

FIG. 6 schematically illustrates a UV radiation sensor 600 according to another embodiment of the present invention. The UV radiation sensor 600 includes a UV-to-visible converter plate 610, an optical interface 620, and a photon detector 630. A UV laser pulse 640 is incident on the UV-to-visible converter plate 610 and excites fluorescent light 650 in the visible range. The optical interface 620 blocks the UV radiation from reaching the photon detector 630, and collects and directs the visible light 650 toward the photon detector 630. The optical interface 620 may also protect the photon detector 630 from damage by the UV radiation. The photon detector 630 generates an electrical signal 660 in response to receiving the visible light 650. The photon detector 630 may be a photodiode, a photomultiplier, a photon counter, or the like, according to various embodiments. The electrical signal 660 generated by the photon detector 630 may be processed by a processing module 670, which may be a part of the control circuitry 432 or may comprise the control circuitry 432.

The UV-to-visible converter plate 610 typically comprises a fluorescent plate. A common problem of currently known UV radiation sensors is that they can exhibit an irreversible drift. For example, the energy reading from such a UV radiation sensor may change over time for the same energy level of UV radiation. In some cases, the cause of the reading drift is a material degradation of the fluorescent plate.

According to some embodiments of the present invention, the UV-to-visible converter plate 610 comprises sapphire. Sapphire demonstrates substantially no or significantly reduced degradation over time when used as a UV radiation sensor component. Sapphire, however, shows temperature sensitivity in its fluorescence profile. Thus, while a sapphire-based UV radiation sensor may have stable energy reading over time at a constant temperature, its energy reading may change as its temperature changes. But unlike the drift problem caused by material degradation, the temperature sensitivity is a reversible process, i.e., the energy reading of a sapphire-based UV radiation sensor will return to its original value when the temperature of the UV radiation sensor returns to its original value.

The term "sapphire" as used herein can refer to either pure or doped sapphire. The response time of a sapphire fluorescent plate may depend on the dopant material and doping concentration. For example, the response time for pure sapphire is about 25 μsec, and the response time for sapphire doped with chromium (Cr) is about 22 msec. Embodiments of the present invention apply to UV radiation sensors using a sapphire fluorescent plate with any type of dopant and any doping concentration. In addition, embodiments of the present invention may include UV radiation sensors using other materials as the fluorescent plate 610. For example, the fluorescent plate 610 may comprise an yttrium oxide (Y2O3) crystal doped with rare-earth ions, such as gadolinium (Gd), europium (Eu), or the like.

Traditionally, the temperature sensitivity problem is solved by stabilizing the temperature of the UV radiation sensor. For example, the temperature of a UV radiation sensor may be stabilized using thermoelectric coolers (TECs) or other active thermal management means. TECs consume electrical power and are bulky, expensive, and noisy. Advantageously, embodiments of the present invention provide solutions that do not require TECs, and therefore are particularly useful in medical systems and other modalities where it is desirable to avoid excessive power consumption, bulk, and/or noise.

According to embodiments of the present invention, the energy reading of the UV radiation sensor can be stabilized by measuring the temperature of the fluorescent plate and compensating the energy reading based on the measured temperature. In some embodiments, the temperature of the fluorescent plate is determined from the temporal profile of the fluorescent signal excited by a UV radiation pulse incident on the fluorescent plate.

Figure 7:
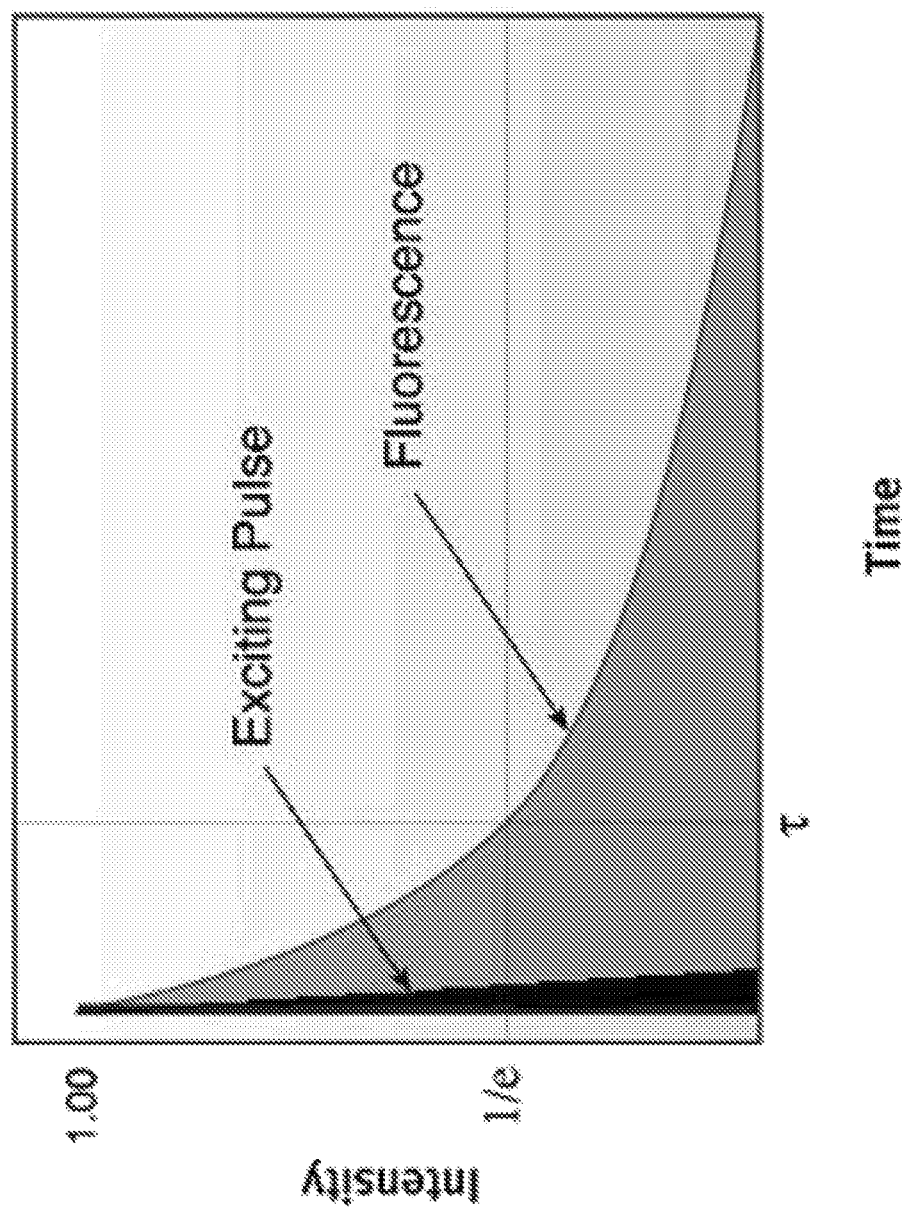
FIG. 7 illustrates an example fluorescence temporal profile showing an exponential decay following excitation with a short UV laser pulse.

FIG. 7 illustrates an example fluorescence decay following excitation with a short UV laser pulse. The fluorescence emitted by the fluorescent plate can decay with time according to $$I(t) = Ae^{-\frac{t}{\tau}}$$

where I(t) is the fluorescence intensity as a function of time, t is time, τ is the fluorescence decay time, and A is the initial fluorescence at t=0. The fluorescence decay time τ, sometimes also referred to as fluorescence lifetime, is the time it takes for the fluorescence intensity I to decay to 1/e or 36.8% of the initial fluorescence A. The fluorescence intensity may also be expressed as $$I(t) = Ae^{-\lambda t}$$

where λ=1/τ is the inverse decay time, and may be referred to as the fluorescent decay constant. The fluorescent decay constant λ may be calculated from the slope of a plot of the natural log of the fluorescent signal I(t) against time t. The fluorescent decay constant λ of a given fluorescent material may have a known correlation with the temperature of that material. The signal I(t) may be referred to as the temporal profile of the fluorescensce intensity. An electrical signal derived by measuring that signal (e.g., the electrical signal 660 discussed elsewhere herein) may have similar form (e.g., temporal profile of electrical signal E(t)=A $e^{-\lambda t}$). The amplitude A of such temporal profile of the electrical signal may be derived by identifying the measured electrical signal intensity at time t=0. The decay constant λ may be obtained by matching a plot of form A $e^{-\lambda t}$ to the actual electrical signal measured and identifying the decay constant λ from that matched plot.

With returning reference to FIG. 6, According to some embodiments, the UV radiation sensor 600 is illuminated with a UV laser pulse 640, and the intensity of the electrical signal 660 generated by the photon detector 630 is recorded as a function of time to obtain the temporal profile of the fluorescent signal. The initial intensity A, also referred herein as the "amplitude," is a function of both the energy E of the incident laser pulse 640 and the temperature T of the fluorescent plate 610. The decay constant λ is a function of the temperature T of the fluorescent plate 610. The processing module 670 can extract the amplitude A and the decay constant λ from the temporal profile of the fluorescent signal 660. The processing module 670 can then use the decay constant λ to determine the temperature T of the fluorescent plate 610.

According to some embodiments, the energy reading of the UV radiation sensor 600 is compensated by a temperature adjustment coefficient k. The temperature adjustment coefficient k is a ratio of two amplitude values:

$$k(T) = \frac{A(T)}{A_{Tref}}$$

where A(T) is the sensor's amplitude reading for a laser pulse of a given energy at current temperature T, and $A_{Tref}$ is the sensor's amplitude reading for a laser pulse of the same energy at a reference temperature Tref. The energy reading E of the UV radiation sensor is calculated as:

$$E = \frac{A(T)}{k(T)}$$

In some embodiments, the processing module 670 may determine the temperature T of the fluorescent plate 610 based on the decay constant λ using a formula or according to an algorithm, or using a look-up table. In some embodiments, the processing module 670 may determine the temperature adjustment coefficient k based on the temperature T using a formula or according to an algorithm, or using a look-up table.

In one embodiment, the processing module 670 determines the temperature T of the fluorescent plate 610 and the temperature adjustment coefficient k using a calibration table established by a prior calibration.

Figure 8:
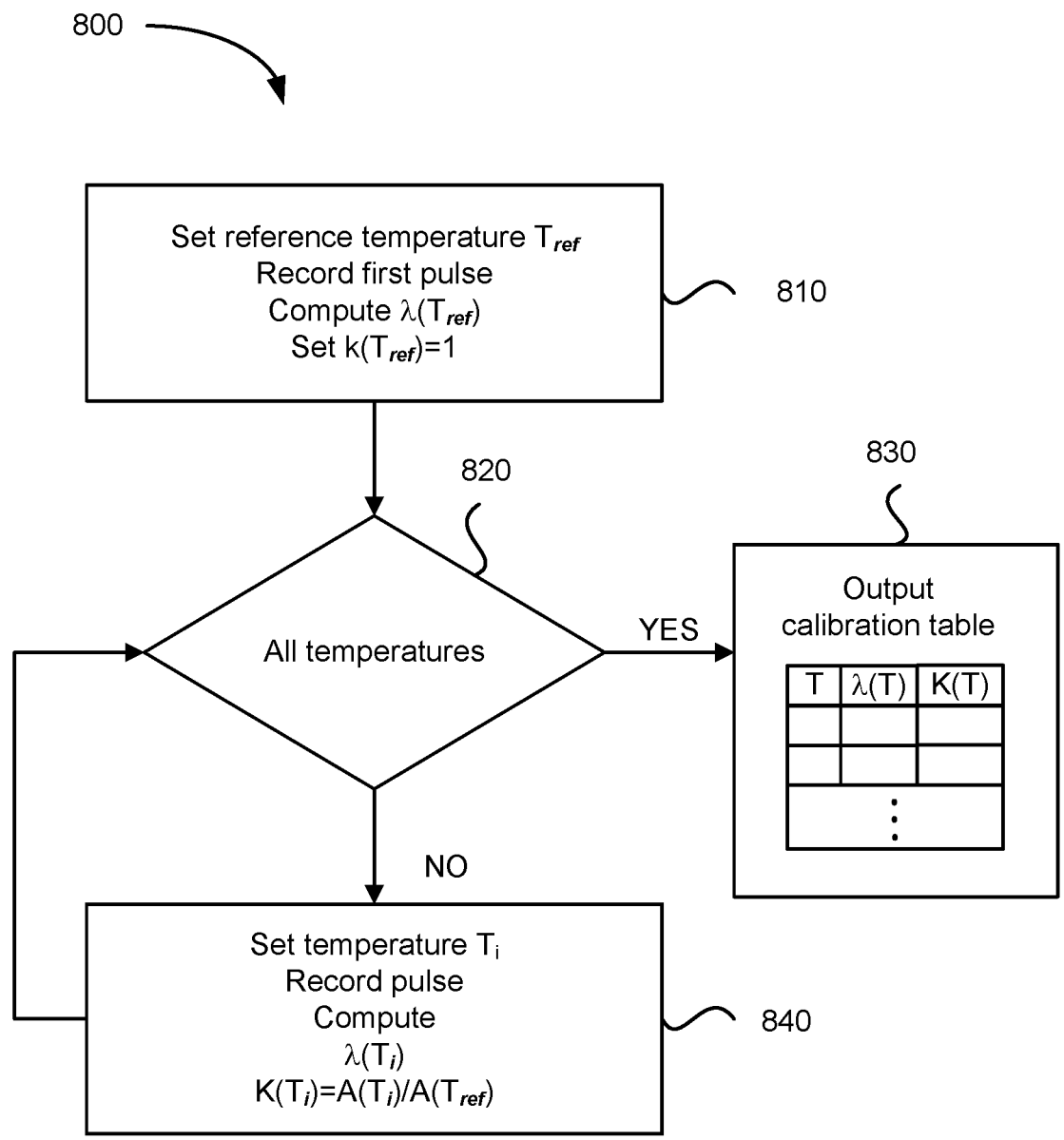
FIG. 8 depicts aspects of an exemplary method of calibrating a UV radiation sensor according to an embodiment of the present invention.
Figure 8A:
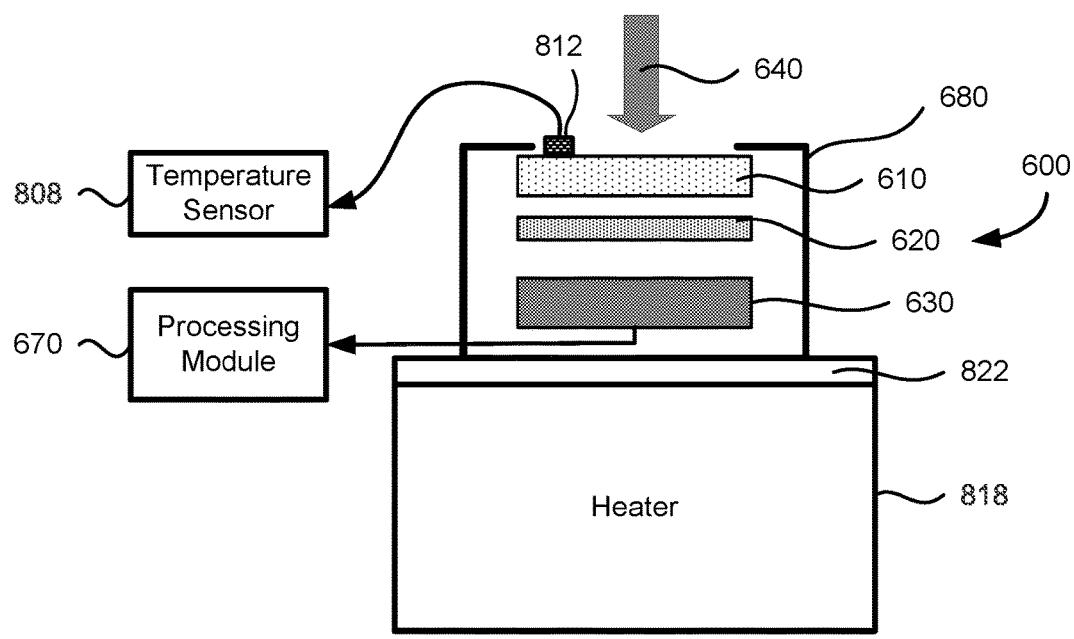
FIG. 8A illustrates schematically an exemplary setup that may be used for calibrating a UV radiation sensor according to an embodiment of the present invention.

FIG. 8 depicts aspects of a method 800 of calibrating a UV radiation sensor, such as sensor 600 shown in FIG. 6, according to an embodiment of the present invention. The calibration 800 can be performed using a UV laser source with known energy value for each laser pulse 640. FIG. 8A illustrates schematically an exemplary set up that may be used for calibrating a UV radiation sensor 600 according to an embodiment the present invention. The UV radiation sensor 600 with a housing 680 may be positioned on a heating surface 822 of a heater 818. The temperature of the UV radiation sensor 600 can be set to one of a predetermined number of temperatures by adjusting the heat output of the heater 818. The temperature of the fluorescent plate 610 may be measured using a temperature sensor 808 that includes a temperature probe 812 attached to the fluorescent plate 610. The temperature probe 812 is attached to the housing 680, with measurement of the temperature of the fluorescent plate 610 occurring after a sufficient amount of time after attachment of the temperature probe 812 to the housing 680 to allow the temperatures of the housing 608 and the temperature probe 812 to be substantially the same. The temperature probe 812 may comprise a thermal couple, a resistive temperature probe, or the like.

Referring to FIG. 8 in conjunction with FIG. 6, the method 800 includes setting the temperature of the UV radiation sensor 600 (specifically including setting the temperature of the fluorescent plate 610) to a reference temperature $T_{ref}$ (specifically including setting the temperature of the fluorescent plate 610 to the reference temperature), and recording the temporal profile of the electrical signal 660 generated by the photon detector 630 in response to an incident laser pulse of known energy, as indicated by step 810. The decay constant $\lambda(T_{ref})$ and the amplitude $A(T_{ref})$ at the reference temperature are extracted from the temporal profile of the electrical signal 660. The temperature adjustment coefficient at the reference temperature k(Tref) can be set to 1.0.

The method 800 further includes determining whether calibration has been performed for all of the predetermined number of temperatures as indicated by step 820. If the answer is "no," the temperature of the UV radiation sensor 600 is set to a next temperature $T_i$ as indicated by step 840. The temporal profile of the electrical signal 660 generated by the photon detector 630 in response to a laser pulse of the known energy incident on the UV radiation sensor 600 is recorded. The decay constant $\lambda(T_i)$ and the amplitude $A(T_i)$ at the current temperature $T_i$ are extracted from the temporal profile of the electrical signal. The temperature adjustment coefficient at the current temperature $k(T_i)$ is computed as, $$k(T_i) = \frac{A(T_i)}{A(T_{ref})}.$$

The method 800 further includes, when calibration has been performed for all of the predetermined number of temperatures, outputting a calibration table as indicated by step 830. In one embodiment, the calibration table comprises three columns, each corresponding to a different one of temperature T, decay constant λ(T), and temperature adjustment coefficient k(T), respectively. Each row corresponds to a respective temperature $T_i$, and includes a corresponding decay constant λ(T) and temperature adjustment coefficient k(T). Once the calibration is done, the calibration table may be used for energy reading adjustment during normal operation of the UV radiation sensor 600 as discussed elsewhere herein (for example by dividing the amplitude A(T) by the temperature adjustment coefficient k(T)). This energy reading may then be used to monitor and/or adjust the treatment as described, for example, with respect to FIG. 4. The steps described with respect to FIG. 8 may be performed at the direction of the processing module 670 of FIG. 6 or control circuitry 432 of FIG. 4.

Figure 9:
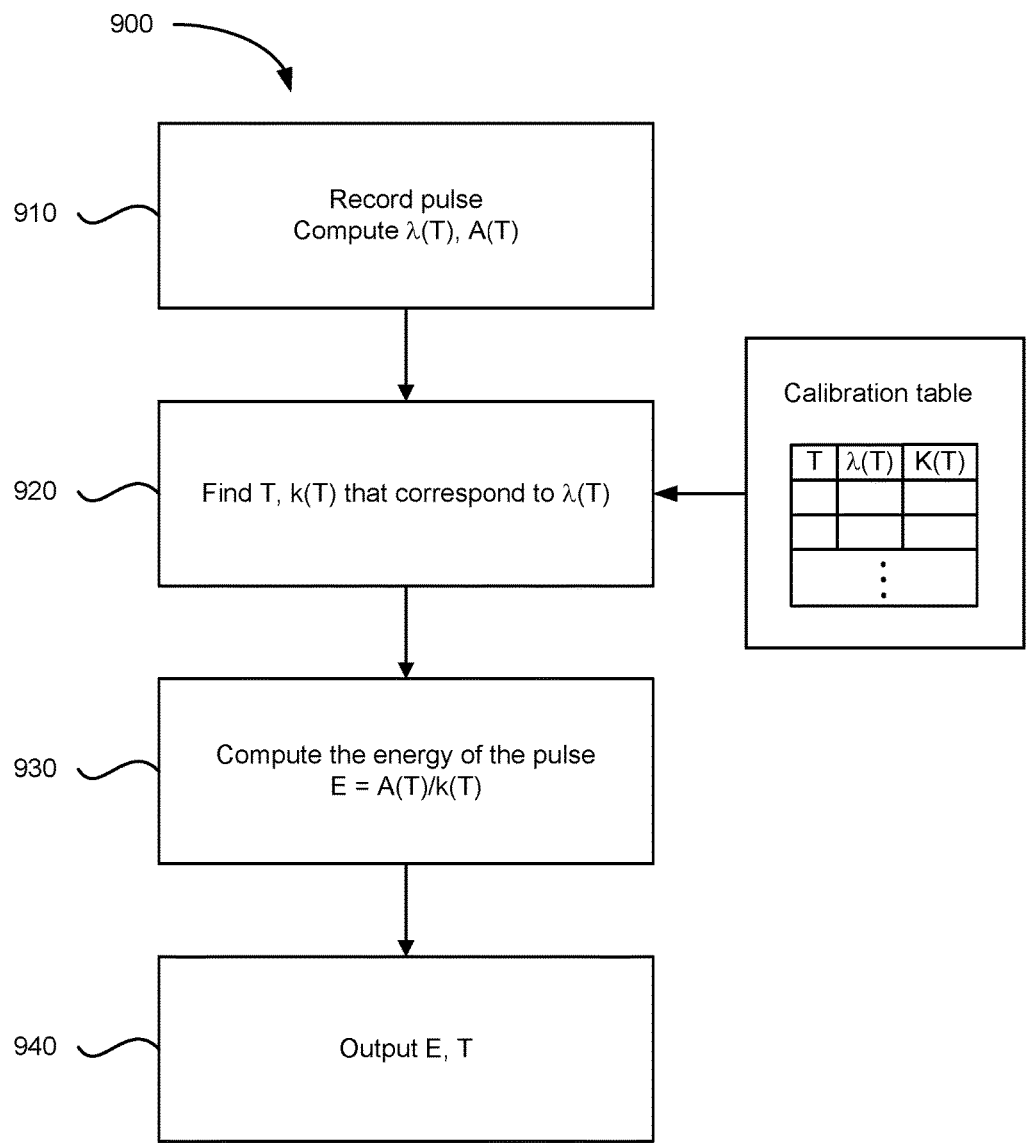
FIG. 9 depicts aspects of an exemplary method for sensor reading adjustment according to an embodiment of the present invention.

FIG. 9 depicts aspects of a method 900 for sensor reading adjustment according to an embodiment of the present invention. With combined reference to both FIG. 6 and FIG. 9, the method 900 includes recording the temporal profile of the electrical signal 660 generated by the photon detector 630 in response to a UV radiation pulse incident on the UV radiation sensor 600, as indicated by step 910. The decay constant λ and the amplitude A are extracted from the temporal profile of the electrical signal 660. The method 900 further includes determining the temperature T of the UV radiation sensor 600 and the temperature adjustment coefficient k(T) corresponding to that temperature based on the decay constant λ by consulting the calibration table, as indicated by step 920. The method 900 further includes computing the energy reading E of the UV radiation sensor 600 by dividing the amplitude A by the temperature adjustment coefficient k(T), as indicated by step 930, and outputting the energy reading E as indicated by step 940. The method 900 may additionally include outputting the temperature T of the UV radiation sensor 600. Subsequently, the energy reading E may be used to adjust the energy output of a future UV radiation pulse. In an example, during a treatment that calls for a plan of particular sequence of laser pulses at given energy values at the treatment plane TP (FIG. 4) by the laser system 430, the laser system 430 may determine that energy values for one or more laser pulses need to be modified as compared with the plan. The method 900 allows for accurate reading of actual energy output by the laser system 430 regardless of temperature variations of the UV radiation sensor 440 during treatment, so that the energy values may be adjusted. A signal (referred to herein as an "energy calibration signal") that indicates the degree to which laser beam energy is to be adjusted may be generated by the laser system 430 (e.g., the control circuitry 432) and provided to the laser system 430 for generation of subsequent laser pulses (i.e., the energy calibration signal may be an internally generated and used signal).

Alternatively, the calibration table may be used to derive a formula for the relationship between the temperature T and the decay constant λ, and a formula for the relationship between the temperature adjustment coefficient k and the temperature T. For example, such formulas may be obtained by any regression methods. The formulas may then be used for determining the temperature T and the temperature adjustment coefficient k based on the decay constant λ at step 920.

In other embodiments, the relationship between the temperature T and the decay constant λ, and the relationship between the temperature adjustment coefficient k and the temperature T may be obtained by other means. Accordingly, an algorithm may be developed for determining the temperature T and the temperature adjustment coefficient k based on the decay constant λ. One of ordinary skill in the art would recognize many variations, alternatives, and modifications.

Figure 10:
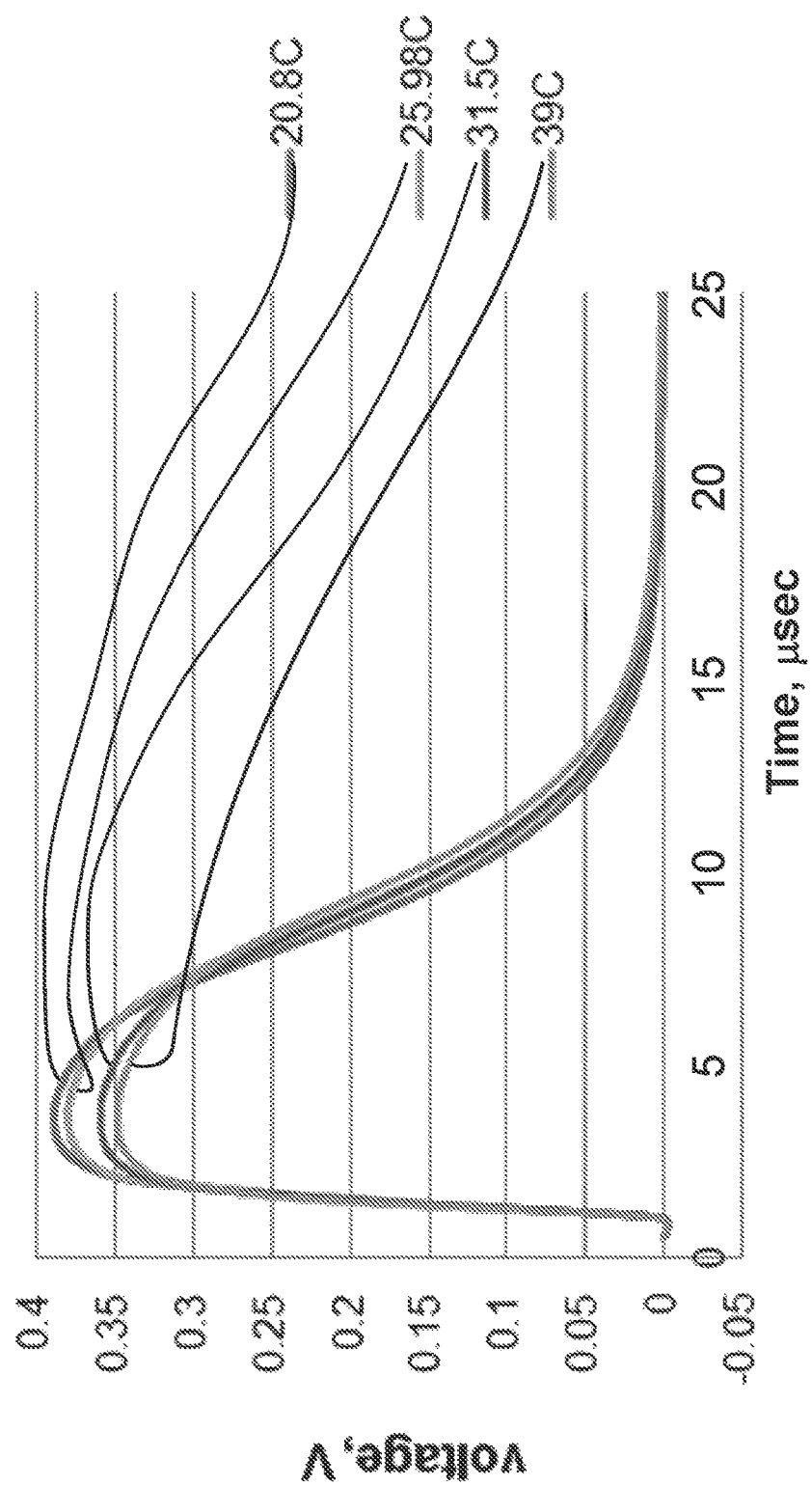
FIG. 10 depicts exemplary voltage profiles generated by the photon detector for five different temperatures according to some embodiments of the present invention.
Figure 11:
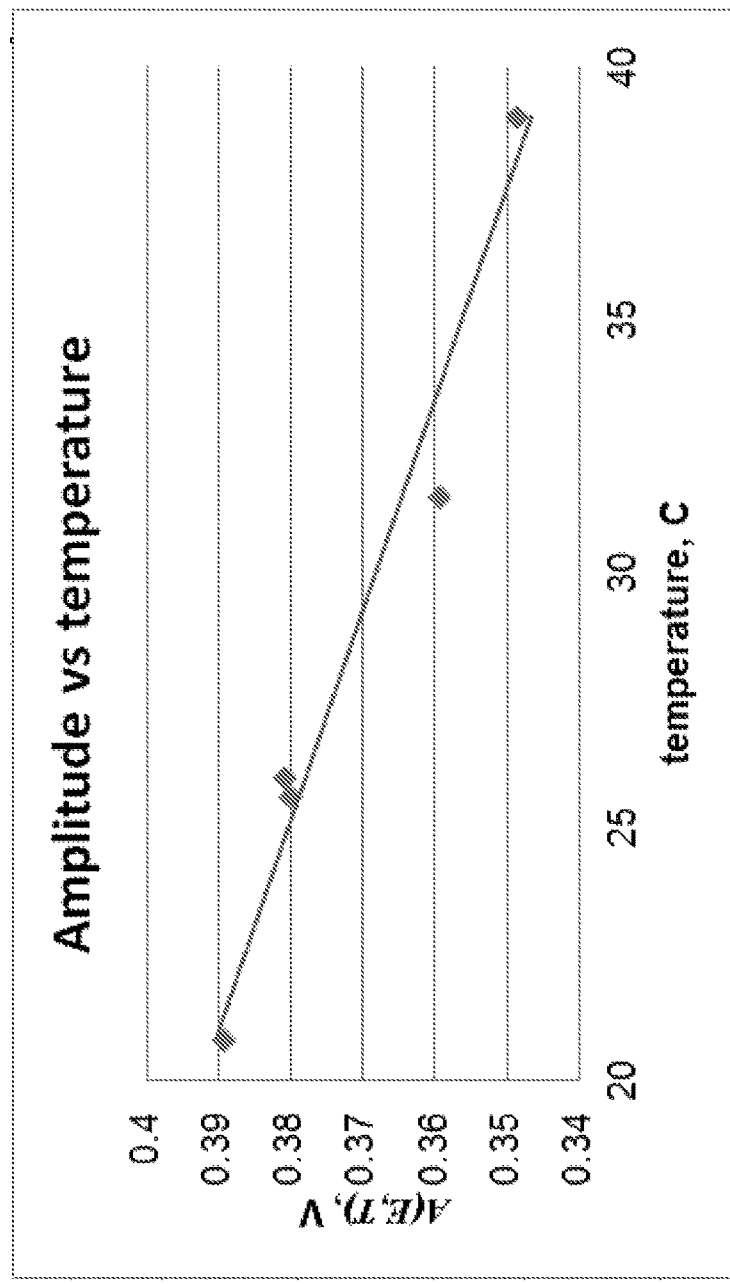
FIG. 11 depicts exemplary amplitudes plotted against temperature according to some embodiments of the present invention.
Figure 12:
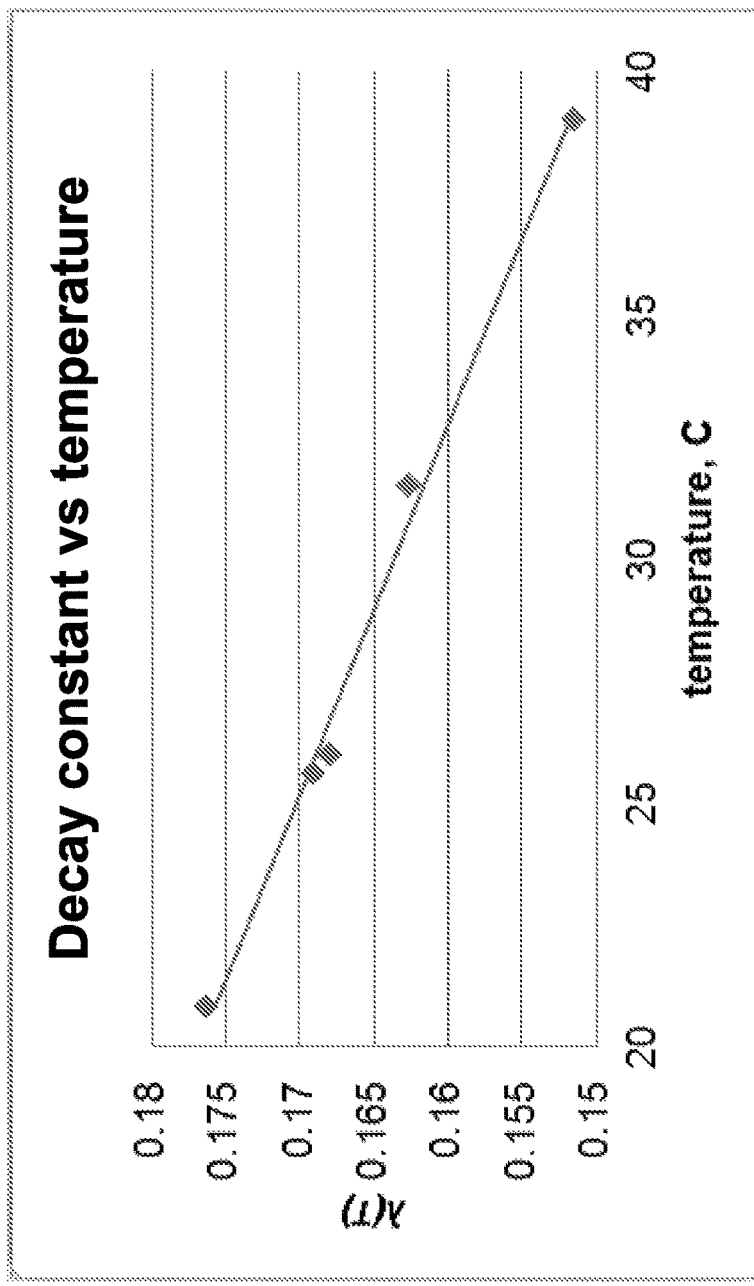
FIG. 12 depicts exemplary decay constants plotted against temperature according to some embodiments of the present invention.

FIG. 10 depicts voltage profiles generated by the photon detector 630 for five different temperatures ranging from about 20° C. to about 40° C. For each temperature, a UV laser pulse with energy E=50 mJ is incident on the UV radiation sensor 600. The processing module 670 extracts the amplitude A and the decay constant λ from the voltage profile for each temperature. FIG. 11 depicts amplitude A vs temperature, as extracted from the voltage profiles shown in FIG. 10. As can be seen, the amplitude is approximately a linear function of the temperature in this temperature range. FIG. 12 depicts decay constant λ vs temperature, as extracted from the voltage profiles shown in FIG. 10. As can be seen, the decay constant is also approximately a linear function of temperature in this temperature range.

Figure 13:
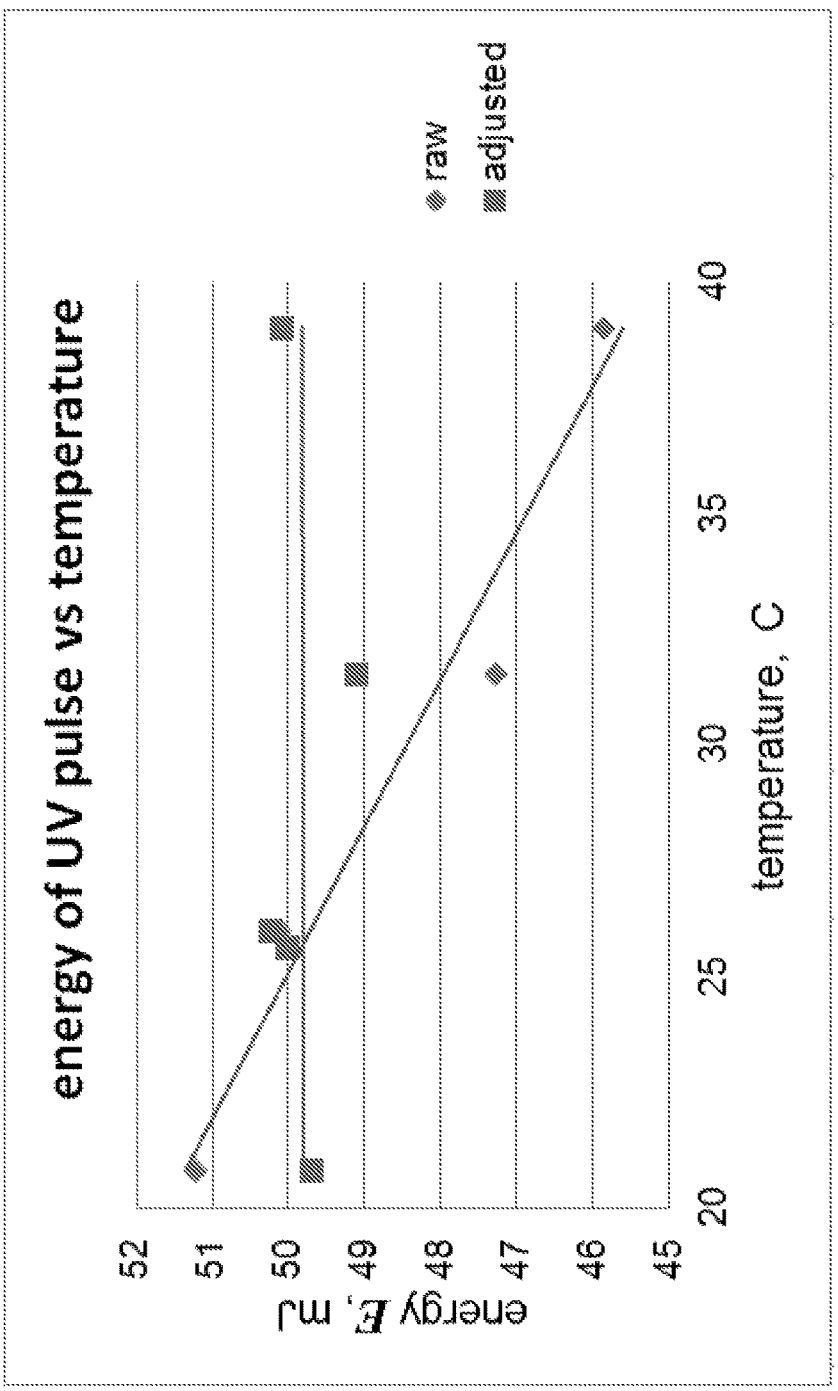
FIG. 13 depicts exemplary raw and temperature compensated energy readings of the UV radiation sensor plotted against temperature according to some embodiments of the present invention.

FIG. 13 depicts the raw (diamonds) and temperature compensated or adjusted (squares) energy reading of the UV radiation sensor 600 vs temperature. The raw energy reading is the amplitude of the respective voltage profile shown in FIG. 10. The temperature compensated energy reading is obtained by dividing the respective raw energy reading by the corresponding temperature adjustment coefficient, as discussed above. The energy reading at 25° C. is considered as a reference point. As can be seen, the raw energy reading decreases as temperature increases, whereas the temperature compensated energy reading is substantially stable as a function of temperature. Thus, embodiments of the present invention provide a UV radiation sensor that may generate substantially temperature-independent energy reading of a UV radiation pulse. Further, because sapphire-based fluorescent plate or rare-earth doped fluorescent materials demonstrate substantially no material degradation or reduction in sensitivity over time, embodiments of the present invention also provide a UV radiation sensor that may generate substantially drift-free energy readings of UV radiation pulses.

In some embodiments, the energy reading of the UV radiation sensor is used as a feedback signal to a laser system in a laser vision treatment system for real-time adjustment of laser pulse energies, for example as illustrated in FIG. 4.

Figure 14:
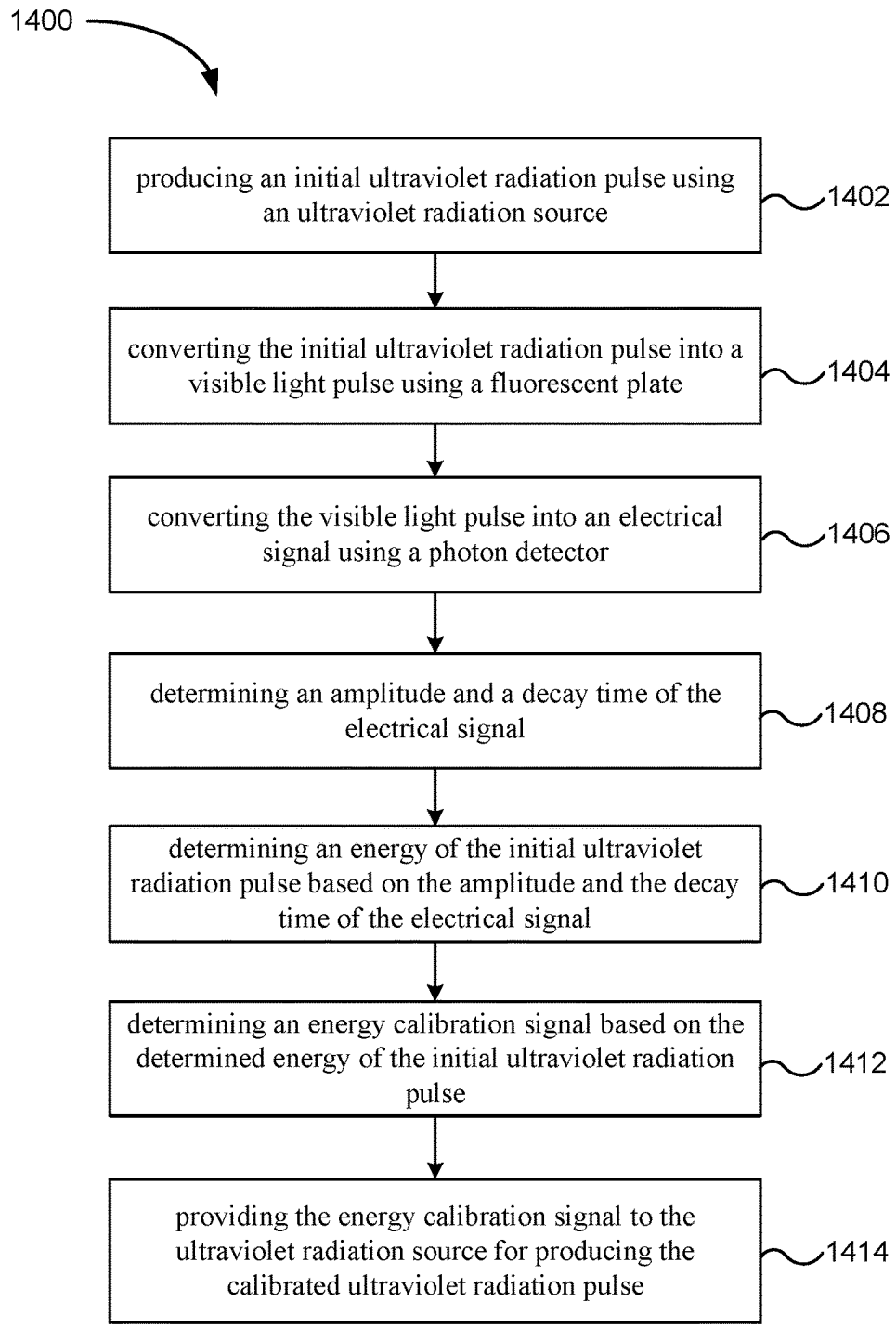
FIG. 14 depicts aspects of an exemplary method of delivering a calibrated UV radiation pulse at a treatment plane during a laser-ablation treatment of a patient's eye according to an embodiment of the present invention.

FIG. 14 depicts aspects of a method 1400 of delivering a calibrated UV radiation pulse at a treatment plane during a laser-ablation treatment of a patient's eye according to an embodiment. As shown here, the method 1400 includes producing an initial ultraviolet radiation pulse using an ultraviolet radiation source as indicated by step 1402, converting the initial ultraviolet radiation pulse into a visible light pulse using a fluorescent plate as indicated by step 1404, and converting the visible light pulse into an electrical signal using a photon detector as indicated by step 1406.

The method 1400 further includes, using a processing module comprising an input for receiving the electrical signal, a processor and a tangible non-transitory computer readable medium, determining an amplitude and a decay time of the electrical signal as indicated by step 1408, and determining an energy of the initial ultraviolet radiation pulse based on the amplitude and the decay time of the electrical signal as indicated by step 1410. In some embodiments, determining the energy of the initial ultraviolet radiation pulse may include determining a temperature of the fluorescent plate based on the decay time of the electrical signal according to a first algorithm, determining a temperature adjustment coefficient based on the temperature of the fluorescent plate according to a second algorithm, and determining the energy of the initial ultraviolet radiation pulse based on the amplitude of the electrical signal and the temperature adjustment coefficient according to a third algorithm. In one embodiment, the energy of the initial ultraviolet radiation pulse is determined by dividing the amplitude of the electrical signal by the temperature adjustment coefficient as discussed above.

The method 1400 further includes determining an energy calibration signal based on the determined energy of the initial ultraviolet radiation pulse as indicated by step 1412, and providing the energy calibration signal to the ultraviolet radiation source for producing the calibrated ultraviolet radiation pulse as indicated by step 1414.

Embodiments of the present invention also include using the UV radiation sensor 600 as a temperature sensor for sensing the absolute temperature of the area surrounding the UV radiation sensor 600. For example, as depicted in FIG. 9, the temperature T of the UV radiation sensor 600 may be output according to the method 900. Thus, the UV radiation sensor 600 may function as a dual sensor for sensing both the energy of a UV laser pulse and the temperature of the area surrounding the UV radiation sensor 600.

According to some embodiments, the sapphire plate may be used as a wireless temperature sensor suitable for use in remote or harsh areas. For example, a collimated UV light beam from a distant light source may be directed to a sapphire plate disposed in a remote area. The fluorescent light in the visible range generated by the sapphire plate may be collected by a telescope-based optical interface and be directed toward a photon detector for further processing and temperature determination, as discussed above. Alternatively, a UV light beam from a distant light source may be directed to the sapphire plate using an optical fiber, and the fluorescent light generated by the sapphire plate may be collected by the same or another optical fiber and be directed to a photon detector for further processing and temperature determination. One of ordinary skill in the art would recognize many variations, alternatives, and modifications.

All patent filings (including patents, patent applications, and patent publications), scientific journals, books, treatises, technical references, and other publications and materials discussed in this application are incorporated herein by reference in their entirety for all purposes.

A variety of modifications are possible within the scope of the present invention. A variety of parameters, variables, factors, and the like can be incorporated into the exemplary method steps or system modules. While the specific embodiments have been described in some detail, by way of example and for clarity of understanding, a variety of adaptations, changes, and modifications will be obvious to those of skill in the art. Although the invention has been described with specific reference to a wavefront system using lenslets, other suitable wavefront systems that measure angles of light passing through the eye may be employed. For example, systems using the principles of ray tracing aberrometry, tscherning aberrometry, and dynamic skiascopy may be used with embodiments of the current invention. The above systems are available from TRACEY Technologies of Bellaire, Tex., Wavelight of Erlangen, Germany, and Nidek, Inc. of Fremont, Calif., respectively. Embodiments of the invention may also be practiced with a spatially resolved refractometer as described in U.S. Pat. Nos. 6,099,125; 6,000,800; and 5,258,791, the full disclosures of which are incorporated herein by reference. Treatments that may benefit from the invention include intraocular lenses, contact lenses, spectacles and other surgical methods in addition to refractive laser corneal surgery.

Each of the calculations or operations discussed herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. While the exemplary embodiments have been described in some detail, by way of example and for clarity of understanding, those of skill in the art will recognize that a variety of modification, adaptations, and changes may be employed.

The methods and apparatuses of the present invention may be provided in one or more kits for such use. The kits may comprise a system for determining a treatment for an eye of a patient, and instructions for use. Optionally, such kits may further include any of the other system components described in relation to the present invention and any other materials or items relevant to the present invention. The instructions for use can set forth any of the methods as described herein.

While the above provides a full and complete disclosure of exemplary embodiments of the present invention, various modifications, alternate constructions and equivalents may be employed as desired. Consequently, although the embodiments have been described in some detail, by way of example and for clarity of understanding, a variety of modifications, changes, and adaptations will be obvious to those of skill in the art. Accordingly, the above description and illustrations should not be construed as limiting the invention, which can be defined by the claims.

What is claimed is:

1. A system comprising:
   an ultraviolet radiation source that produces an initial ultraviolet radiation pulse;
   a fluorescent plate that receives the initial ultraviolet radiation and generates a visible light pulse in response to the initial ultraviolet radiation pulse;
   a photon detector that receives the visible light pulse and generates an electrical signal in response to the visible light pulse received;
   a memory; and
   a processor communicatively coupled to the ultraviolet radiation source; the photon detector and the memory, wherein the processor;
   retrieves calibration data from the memory, and
   determines an energy of the initial ultraviolet radiation pulse by applying the calibration data to an amplitude and a decay time of the electrical signal,
   wherein the processor stores the calibration data in the memory by:
   setting the fluorescent plate to a reference temperature;
   outputting, using the ultraviolet radiation source, a reference ultraviolet radiation pulse having a known energy, the reference ultraviolet radiation pulse being incident on the fluorescent plate;
   receiving a reference electrical signal generated by the photon detector in response to receiving visible light emitted by the fluorescent plate in response to the reference ultraviolet radiation pulse,
   deriving a reference decay constant and a reference amplitude based on the reference electrical signal, and
   determining first calibration data based on a correlation between the reference temperature, the reference decay constant and a reference temperature adjustment coefficient,
   for each of a plurality of calibration temperatures:
   setting the fluorescent plate to a respective calibration temperature from the plurality of calibration temperatures;
   outputting, using the ultraviolet radiation source, a calibration ultraviolet radiation pulse having a known energy for each respective calibration temperature, the calibration ultraviolet radiation pulse being incident on the fluorescent plate;
   receiving a calibration reference signal generated by the photon detector in response to receiving visible light emitted by the fluorescent plate in response to the calibration ultraviolet radiation pulse;
   deriving a calibration decay constant and a calibration amplitude based on the calibration reference signal;
   calculating a calibration temperature adjustment coefficient based on the calibration amplitude and the reference amplitude; and
   determining second calibration data based a correlation between the respective calibration temperature, the calibration decay constant, and the calibration temperature adjustment coefficient, and
   storing, using the memory, the first calibration data and the second as the calibration data.

2. The system of claim 1, wherein the processor further:
   determines an energy calibration signal based on the energy of the initial ultraviolet radiation pulse determined; and
   provides the energy calibration signal to the ultraviolet radiation source for producing an adjusted ultraviolet radiation pulse.

3. The system of claim 1 wherein:
   the calibration data includes data correlating fluorescent plate temperatures with decay constants and temperature adjustment coefficients.

4. The system of claim 3, wherein the processor further determines the energy of the initial ultraviolet radiation pulse based on the amplitude and the decay time of the electrical signal and based on the calibration data by:
   identifying, in the calibration data, a temperature adjustment coefficient that is correlated to the decay time of the electrical signal; and
   determining the energy based on the amplitude of the electrical signal and the temperature adjustment coefficient.

5. The system of claim 1, wherein the processor further: determines a temperature of the fluorescent plate based on the amplitude and the decay time of the electrical signal and based on the calibration data.

6. The system of claim 1, further comprising an optical interface positioned between the fluorescent plate and the photon detector for blocking ultraviolet radiation and transmitting visible light.

7. The system of claim 1, wherein a position of the fluorescent plate correlates to a treatment plane.

8. A method comprising:
receiving, at a fluorescent plate, an initial ultraviolet radiation pulse produced by an ultraviolet radiation source;
generating, by the fluorescent plate, a visible light pulse in response to the initial ultraviolet radiation pulse;
receiving, at a photon detector, the visible light pulse;
generating, at the photon detector, an electrical signal in response to the visible light pulse;
retrieving calibration data from a memory; and
determining an energy of the initial ultraviolet radiation pulse by applying the calibration data to an amplitude and a decay time of the electrical signal,
wherein the calibration data is stored in the memory by:
setting the fluorescent plate to a reference temperature;
outputting, using the ultraviolet radiation source, a reference ultraviolet radiation pulse having a known energy, the reference ultraviolet radiation pulse being incident on the fluorescent plate;
receiving a reference electrical signal generated by the photon detector in response to receiving visible light emitted by the fluorescent plate in response to the reference ultraviolet radiation pulse,
deriving a reference decay constant and a reference amplitude based on the reference electrical signal, and
determining first calibration data based on a correlation between the reference temperature, the reference decay constant and a reference temperature adjustment coefficient,
for each of a plurality of calibration temperatures:
setting the fluorescent plate to a respective calibration temperature from the plurality of calibration temperatures;
outputting, using the ultraviolet radiation source, a calibration ultraviolet radiation pulse having a known energy for each respective calibration temperature, the calibration ultraviolet radiation pulse being incident on the fluorescent plate;
receiving a calibration reference signal generated by the photon detector in response to receiving visible light emitted by the fluorescent plate in response to the calibration ultraviolet radiation pulse;
deriving a calibration decay constant and a calibration amplitude based on the calibration reference signal;
calculating a calibration temperature adjustment coefficient based on the calibration amplitude and the reference amplitude; and
determining second calibration data based a correlation between the respective calibration temperature, the calibration decay constant, and the calibration temperature adjustment coefficient, and
storing, using the memory, the first calibration data and the second as the calibration data.

9. The method of claim 8, further comprising:
determining an energy calibration signal based on the energy of the initial ultraviolet radiation pulse determined; and
producing an adjusted ultraviolet radiation pulse based on the energy calibration signal.

10. The method of claim 8, wherein:
the calibration data includes data correlating fluorescent plate temperatures with decay constants and temperature adjustment coefficients.

11. The method of claim 10, wherein determining the energy of the initial ultraviolet radiation pulse based on the amplitude and the decay time of the electrical signal and based on the calibration data comprises:
identifying, in the calibration data, a temperature adjustment coefficient that is correlated to the decay time of the electrical signal; and
determining the energy based on the amplitude of the electrical signal and the temperature adjustment coefficient.

12. The method of claim 8, further comprising determining a temperature of the fluorescent plate based on the amplitude and the decay time of the electrical signal and based on the calibration data.

13. The method of claim 8, wherein a position of the fluorescent plate correlates to a treatment plane.

14. A sensor comprising:
a first communication interface that is communicatively coupled to a fluorescent plate positioned to receive an initial ultraviolet radiation pulse produced by an ultraviolet radiation source, wherein the fluorescent plate generating a visible light pulse in response to the initial ultraviolet radiation pulse;
a second communication interface that is communicatively coupled to a photon detector positioned to receive the visible light pulse for generating an electrical signal in response to the visible light pulse;
a memory; and
a processor communicatively coupled to the first communication interface, the second communication interface and the memory, wherein the processor:
retrieves calibration data from the memory, and
determines an energy of the initial ultraviolet radiation pulse by applying the calibration data to an amplitude and a decay time of the electrical signal,
wherein the processor stores the calibration data in the memory by:
setting, using the first communication interface, the fluorescent plate to a reference temperature;
outputting, using the ultraviolet radiation source, a reference ultraviolet radiation pulse having a known energy, the reference ultraviolet radiation pulse being incident on the fluorescent plate;
receiving, using the second communication interface, a reference electrical signal generated by the photon detector in response to receiving visible light emitted by the fluorescent plate in response to the reference ultraviolet radiation pulse,
deriving a reference decay constant and a reference amplitude based on the reference electrical signal, and
determining first calibration data based on a correlation between the reference temperature, the reference decay constant and a reference temperature adjustment coefficient,
for each of a plurality of calibration temperatures:
setting, using the first communication interface, the fluorescent plate to a respective calibration temperature from the plurality of calibration temperatures;
outputting, using the ultraviolet radiation source, a calibration ultraviolet radiation pulse having a known energy for each respective calibration temperature, the calibration ultraviolet radiation pulse being incident on the fluorescent plate;

receiving, using the second communication interface, a calibration reference signal generated by the photon detector in response to receiving visible light emitted by the fluorescent plate in response to the calibration ultraviolet radiation pulse;

deriving a calibration decay constant and a calibration amplitude based on the calibration reference signal;

calculating a calibration temperature adjustment coefficient based on the calibration amplitude and the reference amplitude; and determining second calibration data based a correlation between the respective calibration temperature, the calibration decay constant, and the calibration temperature adjustment coefficient, and storing, using the memory, the first calibration data and the second as the calibration data.

15. The sensor of claim 14, wherein the processor further:

determines an energy calibration signal based on the energy of the initial ultraviolet radiation pulse determined; and provides the energy calibration signal to the ultraviolet radiation source for producing an adjusted ultraviolet radiation pulse.

16. The sensor of claim 14, wherein a position of the fluorescent plate correlates to a treatment plane.

* * * * *